US012257024B1

(12) United States Patent
Miller et al.

(10) Patent No.: US 12,257,024 B1
(45) Date of Patent: Mar. 25, 2025

(54) WEARABLE STRESS TESTING DEVICE

(71) Applicant: Tula Health, Inc., Kaysville, UT (US)

(72) Inventors: Devin Warner Miller, Morgan, UT (US); David Rich Miller, Morgan, UT (US); Jeffrey Michael Lee, Morgan, UT (US)

(73) Assignee: JRE Star Investment Holdings, LLC, Farmington, UT (US)

( * ) Notice: Subject to any disclaimer, the term of this patent is extended or adjusted under 35 U.S.C. 154(b) by 315 days.

(21) Appl. No.: 17/157,478

(22) Filed: Jan. 25, 2021

Related U.S. Application Data

(62) Division of application No. 14/697,452, filed on Apr. 27, 2015, now Pat. No. 10,898,075.

(60) Provisional application No. 61/984,039, filed on Apr. 25, 2014.

(51) Int. Cl.
| | |
|---|---|
| *A61B 5/00* | (2006.01) |
| *A61B 5/0205* | (2006.01) |
| *A61B 5/11* | (2006.01) |
| *A61B 5/16* | (2006.01) |
| *A61B 5/1455* | (2006.01) |

(52) U.S. Cl.
CPC .......... *A61B 5/0022* (2013.01); *A61B 5/0205* (2013.01); *A61B 5/1118* (2013.01); *A61B 5/165* (2013.01); *A61B 5/6823* (2013.01); *A61B 5/6824* (2013.01); *A61B 5/6831* (2013.01); *A61B 5/7246* (2013.01); *A61B 5/14551* (2013.01); *A61B 5/4848* (2013.01); *A61B 5/7275* (2013.01)

(58) Field of Classification Search
CPC ... A61B 5/0022; A61B 5/0205; A61B 5/1118; A61B 5/6823; A61B 5/6824; A61B 5/7246; A61B 5/14551; A61B 5/4848; A61B 5/7275
USPC .................................................. 600/300–301
See application file for complete search history.

(56) References Cited

U.S. PATENT DOCUMENTS

| | | | |
|---|---|---|---|
| 6,605,038 B1 | 8/2003 | Teller et al. | |
| 7,033,321 B1 | 4/2006 | Sarvazyan | |
| 7,285,090 B2 | 10/2007 | Stivoric et al. | |
| 7,539,533 B2 * | 5/2009 | Tran ................... | A61B 5/02108 600/509 |
| 7,558,622 B2 | 7/2009 | Tran | |

(Continued)

OTHER PUBLICATIONS

U.S. Appl. No. 17/157,475, dated Mar. 28, 2023, Office Action.

(Continued)

*Primary Examiner* — Shirley X Jian
(74) *Attorney, Agent, or Firm* — RAY QUINNEY & NEBEKER; Thomas L. Lingard

(57) ABSTRACT

Described herein are apparatuses and methods for measuring stress with a wearable device. In one apparatus, a wearable device includes a housing formed and shaped to affix to a user, a sensor integrated into the housing operable to engage a body of the user to take physiological measurements of the user over a threshold period of time to obtain physiological data, and a processing device coupled to the sensor. The processing device may be operable to receive, from the sensor, a first physiological data; receive, from the sensor, a second physiological data; determine a correlation between the first physiological data and the second physiological data; and determine a stress level of a bodily system of the user based on the correlation.

20 Claims, 23 Drawing Sheets

(56) References Cited

U.S. PATENT DOCUMENTS

| | | | |
|---|---|---|---|
| 7,594,889 B2 | 9/2009 | St. Ores | |
| 7,689,437 B1 | 3/2010 | Teller et al. | |
| 7,698,157 B2 | 4/2010 | Ghouri | |
| 7,959,567 B2 | 6/2011 | Stivoric et al. | |
| 8,103,333 B2* | 1/2012 | Tran | A61B 5/7405 600/509 |
| 8,157,730 B2* | 4/2012 | LeBoeuf | G16H 10/60 600/595 |
| 8,271,296 B2 | 9/2012 | Li | |
| 8,323,188 B2* | 12/2012 | Tran | A61B 5/316 600/300 |
| 8,323,191 B2 | 12/2012 | Bodlaender et al. | |
| 8,398,546 B2 | 3/2013 | Pacione et al. | |
| 8,529,447 B2 | 9/2013 | Jain et al. | |
| 8,538,510 B2 | 9/2013 | Toledo et al. | |
| 8,540,629 B2 | 9/2013 | Jain et al. | |
| 8,617,067 B2 | 12/2013 | Jain et al. | |
| 8,622,899 B2 | 1/2014 | Jain et al. | |
| 8,622,901 B2 | 1/2014 | Jain et al. | |
| 8,684,900 B2* | 4/2014 | Tran | A61B 5/7465 600/3 |
| 8,702,607 B2* | 4/2014 | LeBoeuf | A61B 5/415 600/595 |
| 8,821,416 B2 | 9/2014 | Johansson et al. | |
| 8,862,211 B2 | 10/2014 | Toledo et al. | |
| 8,870,766 B2 | 10/2014 | Stivoric et al. | |
| 8,961,413 B2 | 2/2015 | Teller et al. | |
| 8,961,414 B2 | 2/2015 | Teller et al. | |
| 8,961,415 B2 | 2/2015 | LeBoeuf et al. | |
| 9,028,405 B2 | 5/2015 | Tran | |
| 9,033,875 B2 | 5/2015 | Teller et al. | |
| 9,307,941 B2 | 4/2016 | Johansson et al. | |
| 2005/0192488 A1 | 9/2005 | Bryenton et al. | |
| 2005/0234356 A1 | 10/2005 | Rowlandson et al. | |
| 2005/0245839 A1 | 11/2005 | Stivoric et al. | |
| 2006/0058593 A1 | 6/2006 | Drinan et al. | |
| 2006/0115429 A1 | 6/2006 | Afeyan et al. | |
| 2007/0099203 A1 | 5/2007 | Zhang | |
| 2007/0219059 A1 | 9/2007 | Schwartz et al. | |
| 2007/0273504 A1 | 11/2007 | Tran | |
| 2007/0276270 A1 | 11/2007 | Tran | |
| 2008/0001735 A1 | 1/2008 | Tran | |
| 2008/0039700 A1 | 2/2008 | Drinan et al. | |
| 2008/0051843 A1 | 2/2008 | Li et al. | |
| 2008/0146890 A1 | 6/2008 | LeBoeuf et al. | |
| 2008/0146892 A1 | 6/2008 | LeBoeuf et al. | |
| 2008/0270071 A1* | 10/2008 | Marvasti | G05B 23/024 702/179 |
| 2009/0005657 A1 | 1/2009 | Bodlaender et al. | |
| 2009/0088611 A1* | 4/2009 | Buschmann | A61B 5/6817 600/301 |
| 2009/0227876 A1 | 9/2009 | Tran | |
| 2009/0318820 A1 | 12/2009 | Toledo et al. | |
| 2011/0301441 A1 | 12/2011 | Bandic et al. | |
| 2012/0095352 A1 | 4/2012 | Tran | |
| 2012/0123232 A1 | 5/2012 | Najarian et al. | |
| 2012/0150052 A1* | 6/2012 | Buchheim | A61B 5/721 600/500 |
| 2012/0245439 A1 | 9/2012 | Andre et al. | |
| 2012/0289791 A1* | 11/2012 | Jain | A61B 5/02055 600/301 |
| 2012/0289794 A1 | 11/2012 | Jain et al. | |
| 2013/0041290 A1* | 2/2013 | Kording | A61B 5/117 600/595 |
| 2013/0172691 A1* | 7/2013 | Tran | A61B 5/0022 600/595 |
| 2014/0018641 A1 | 1/2014 | Yoshino et al. | |
| 2014/0031709 A1 | 1/2014 | Toledo et al. | |
| 2014/0035761 A1 | 2/2014 | Burton | |
| 2014/0058280 A1* | 2/2014 | Chefles | G16H 40/67 600/509 |
| 2014/0128715 A1* | 5/2014 | Banet | G16H 10/60 600/513 |
| 2014/0143064 A1 | 5/2014 | Tran | |
| 2014/0221792 A1 | 8/2014 | Miller et al. | |
| 2015/0120205 A1 | 4/2015 | Jeon et al. | |
| 2015/0126845 A1 | 5/2015 | Jin et al. | |
| 2015/0289820 A1 | 10/2015 | Miller et al. | |
| 2015/0305675 A1 | 10/2015 | Miller et al. | |
| 2016/0051191 A1 | 2/2016 | Miller et al. | |
| 2016/0128627 A1* | 5/2016 | Demos | A61B 5/0075 600/473 |

OTHER PUBLICATIONS

U.S. Appl. No. 17/157,475, dated Nov. 9, 2023, Office Action.
U.S. Appl. No. 17/157,475, dated Jan. 3, 2024, Office Action.
U.S. Appl. No. 17/157,475, dated Mar. 7, 2024, Office Action.
U.S. Appl. No. 17/157,475, dated Jul. 24, 2024, Notice of Allowance.
U.S. Appl. No. 14/697,452, dated Jun. 27, 2016, Office Action.
U.S. Appl. No. 14/697,452, Mar. 9, 2017, Office Action.
U.S. Appl. No. 14/697,452, dated Jul. 19, 2018, Office Action.
U.S. Appl. No. 14/697,452, Mar. 21, 2019, Office Action.
U.S. Appl. No. 14/697,452, dated Nov. 18, 2019, Office Action.
U.S. Appl. No. 14/697,452, dated Sep. 3, 2020, Notice of Allowance.
U.S. Appl. No. 14/697,452, dated Jan. 6, 2021, Issue Notification.
U.S. Appl. No. 17/157,475, dated Oct. 18, 2024, Notice of Allowance.

* cited by examiner

WEARABLE STRESS TESTING DEVICE

RELATED APPLICATIONS

This application is a divisional of U.S. patent application Ser. No. 14/697,452 filed Apr. 27, 2015 and titled "WEARABLE STRESS TESTING DEVICE" which claims the benefit of U.S. Provisional Application No. 61/984,039 filed Apr. 25, 2014, the entire contents of which are incorporated by reference.

BACKGROUND

Cardiovascular ailments, such as high blood pressure, coronary artery disease, congestive heart failure, arrhythmia (Atrial fibrillation), and so forth pose a significant health threat to millions of individuals. Early and proper diagnosis of such ailments can be beneficial in placing the patient on the road to recovery. Over the years, a variety of techniques have been developed to diagnose such conditions. Some of these techniques involve stressing the patient's cardiovascular system by having the patient to physically exercise. For example, one common stress test is to place various monitors on the patient and then have the patient to walk and run on a treadmill. A stress test or a treadmill test can help a doctor diagnose an individual's heart handles exertion. While such tests may be a generally accepted procedure for diagnosing cardiovascular ailments, they can be cumbersome and inconvenient. Additionally, many patients may not be able to exercise, and the exercise itself may limit the kinds of physiological measurements that can be acquired. For example, various types of diagnostic equipment may not be compatible with testing a patient without using a treadmill.

BRIEF DESCRIPTION OF THE DRAWINGS

Features and advantages of the disclosure will be apparent from the detailed description which follows, taken in conjunction with the accompanying drawings, which together illustrate, by way of example, features of the disclosure; and wherein.

Figure 1:
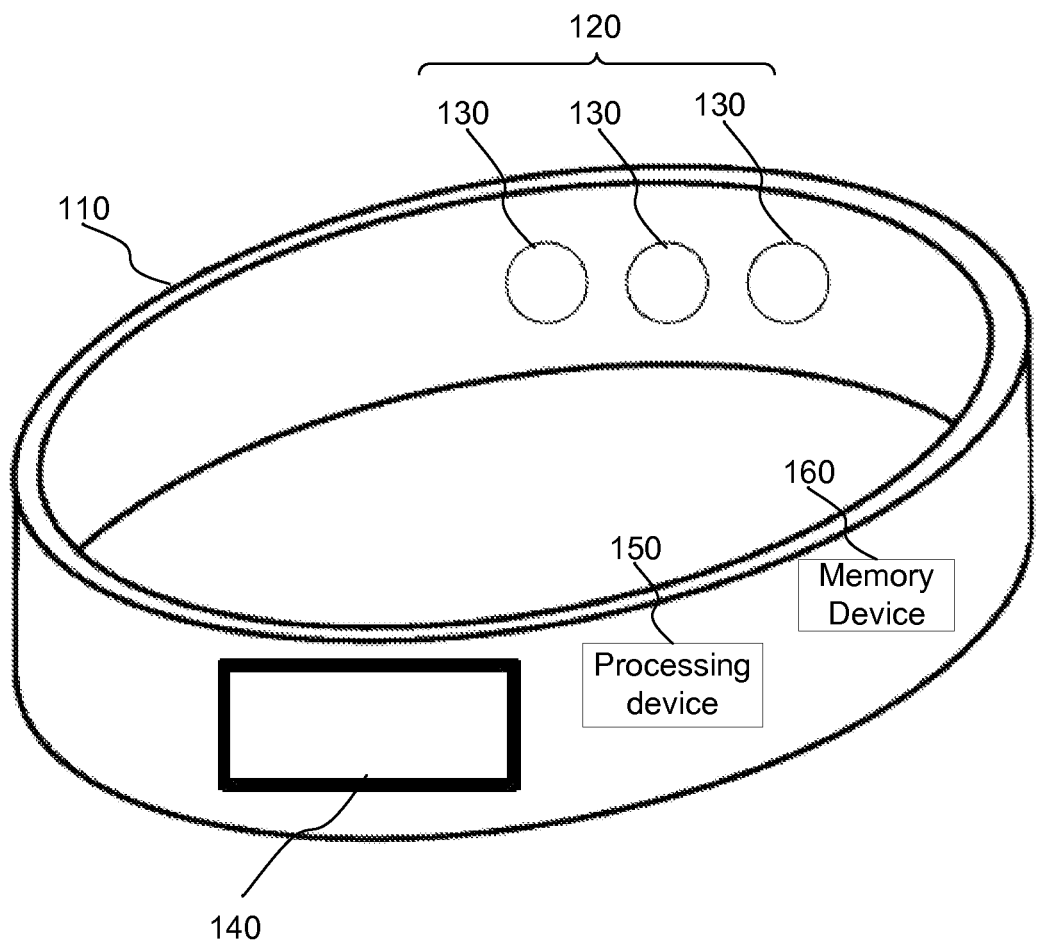
FIG. 1 depicts a wearable stress-testing device according to one embodiment.

Reference will now be made to the exemplary embodiments illustrated, and specific language will be used herein to describe the same. It will nevertheless be understood that no limitation of the scope of the invention is thereby intended.

DETAILED DESCRIPTION

Monitoring how a heart of an individual performs under various conditions can enable individuals to be monitored for cardiovascular infirmities, such as congestive heart failure (CHF). A cardiac stress test can be performed to measure the response of the heart to an increase in workload or stress to the heart. Using a stress test, the heart can be induced to beat faster than normal or change a volume of blood that the heart moves throughout a cardiovascular system of a body of an individual. The inducted stress may reveal abnormalities in how the heart may be functioning. A cardiac stress test may generally be performed after a patient has experienced symptoms or when the patient may be at high risk for heart disease. Typically, cardiac stress can go unrecognized until a patient experiences adverse symptom or suffers a life-threatening event, such as a heart attack. For example, a cardiac condition of a patient can be asymptomatic, e.g., the condition can go undetected, until a major cardiac event (such as a major heart attack) occurs and indicates that the patient has a cardiac condition.

Normally, a fixed stress test may be performed by attaching a device to an individual to monitor the stress level of the individual in a controlled clinical environment. However, the fixed stress test can be limited in diagnostic ability because of the brevity and infrequency of the fixed stress test. Another problem with the fixed stress test can be that some individuals may not be able to undertake the test. The embodiments described herein may address the above noted deficiency by providing a wearable device that can monitor an individual during a variety of activities and under a variety of conditions. In one example, the wearable device can be a wearable stress-testing device. Stress-testing can include testing one or more stresses on an individual including one or more physiological stresses, one or more psychological stresses, and so forth. In one example, the wearable device can take measurements relating to the body of the individual and/or an environment approximate or adjacent an individual. A measurement can be an act of taking a measurement using a sensor, data collected or associated with a measurement of a sensor, an amount or extent of a parameter determined by measuring the parameter, a unit associated with a type of measurement, or a combination thereof.

Measurements related to the body of the individuals may include motion and movement of the body (e.g., acceleration, speed, motion, position, location, etc.), hydration of the body, a number of heart beats of the body, and so forth. One advantage of the wearable stress-testing device can be to perform a stress test on an individual that may not be performed under the typical clinical stress test conditions. Another advantage of the wearable stress test can be early and accurate detection of cardiac stress to enable an individual to avoid adverse symptoms or life-threatening events.

The wearable stress-testing device can be used to perform a variety of different stress tests and used in a variety of conditions. In one example, the wearable stress-testing device can be used for a treadmill stress test. During a treadmill stress test, an individual may walk or jog on a treadmill while the wearable stress-testing device monitors an electrocardiography (ECG) of the individual. An ECG can be a graphic outline of the movement of a heart of the individual. For example, the ECG can illustrate a motion of the walls of the heart of the individual and a pumping action when the heart may be under stressed conditions. The individual may walk or jog on the treadmill while being monitored by the wearable stress-testing device to see how far the individual can walk or jog. The wearable stress-testing device can also determine when the individual develops chest pain or changes in an ECG of the individual during the walk or jog. The chest pains or changes in the ECG can indicate that the heart of the individual may not be getting enough blood or pumping enough blood through the body of the individual.

In another example, the wearable stress-testing device can be used for a Dobutamine or Adenosine stress test. The Dobutamine or Adenosine stress test may typically be used for individuals who may not be able to exercise. During the Dobutamine or Adenosine stress test, a drug may be given to the individual to make the heart of the individual respond as if the person were exercising. The wearable stress-testing device can monitor the stress on the heart of the individual during the period the drug affects the heart of the individual.

In one example, a portable and/or wearable stress-testing device can continuously monitor (e.g., uninterrupted measurements or measurements without gaps), semi-continuously monitor (measurement instants with minimal or negligible gaps between measurements), or periodically monitor of a cardiac condition, cardiac health, cardiac or physical performance, cardiac or physical output, and/or overall health of an individual. The wearable stress-testing device can monitor the individual on a continuous or frequent basis under a variety conditions (e.g., day-to-day conditions, conditions outside of a controlled clinical environment, etc.). Continuous, semi-continuous, or periodic testing over a period of hours, days, weeks, months, or years can provide a cardiac performance assessment of an individual at: various times of the day, various levels of exertion, various levels of healthiness and wellness circumstances (e.g., when an individual may be healthy, has a cold or flu, and so forth), various levels of fluid retention, various environmental conditions (hot, cold, humid), and under various other environments and conditions. For example, an individual with a cardiac condition can be asymptomatic while the individual may be healthy and have a high or increased risk of suffering a cardiac event when the individual becomes sick, such as when the individual contracts the flu. An advantage of the wearable stress-testing device can be that while fixed stress test may be performed in a controlled clinical environment and can have limited diagnostic effectiveness because of the brevity and infrequency of the stress test, the wearable stress-testing device can monitor under a variety of conditions and on a continuous basis.

FIG. 1 depicts a wearable stress-testing device 110 according to one embodiment. FIG. 1 illustrates that the portable or wearable stress-testing device 110 can be a wristband, headband, armband, chest band, leg band, strap, piece of clothing, accessory, or other object attached or coupled to an individual at a desired location on the individual. The wearable stress-testing device 110 can include a sensor 130 or a sensor array 120 with one or more sensors 130. In one example, the sensor 130 can be a physiological sensor. The physiological sensor can include: a pulse oximeter, an electrocardiography (ECG) sensor, a fluid level sensor, an oxygen saturation sensor, a body temperature sensor, a plethysmograph sensor, a respiration sensor, a breath rate sensor, a cardiac sensor, or other physiological sensors. The wearable stress-testing device can include a display 140 to show information to a user or a third party. Information shown on the display 140 may include a heart rate, a breathing rate, a medical alert, a notice to take medication, and/or other information. In one example, the display 140 can be a touch screen and can display a graphical user interface (GUI) to receive information. In another example, the wearable stress-testing device 110 can include a data port or wireless communications device (as discussed in the proceeding paragraphs) to receive information from another device. The wearable stress-testing device 110 may receive and/or display information, such as health status information, health risk information, medication information, and other information. The wearable stress-testing device can include a processor or processing device 150 to analyze or process measurements, received information, user input data, and/or other types of data.

In one example, the wearable stress-testing device 110 can monitor stress on a respiratory system of the individual. For example, the wearable stress-testing device 110 can use the sensor 130, such as an oxygen saturation sensor, to monitor the stress on a respiratory system of the individual. In another example, the wearable stress-testing device 110 can use one or more sensors 130 in the sensor array 120 to monitor stress on a plurality of systems of an individual, such as a biological system or a body system. The biological system may include a respiratory system, a cardiovascular system, a nervous system, an integumentary system, a urinary system, an excretory system, a digestive system, an immune system, an endocrine system, a lymphatic system, a muscular system, a skeletal system, a reproductive system, and other systems. The body system may include two or more organs working together in the execution of a specific bodily function, e.g., a neuroendocrine system, a musculoskeletal system, etc. For example, the wearable stress-testing device 110 can monitor stress on the cardiac system of an individual using a blood pressure sensor of the sensor array 120 and can monitor the stress on the respiratory system of the individual using an oxygen saturation sensor of the sensor array 120. In another example, the wearable stress-testing device 110 can monitor biological systems, organs, body parts, body system, or other areas of an individual. In another example, the wearable stress-testing device 110 can monitor or aggregate stress measurements from the sensors of the sensor array with other measurements, such as a lung capacity of an individual, a hematocrit (HCT), an oxygen saturation level, and/or or other medical measurements. In another example, the wearable stress-testing device 110 can analyze the aggregated measurements to determine stress on one or more biological systems, organs, body parts, and/or body system and use the aggregated measurements to determine medical conditions.

The sensor 130 can be an environmental sensor, such as a humidity sensor, an ambient temperature sensor, an altitude sensor, a barometer, and/or another environmental sensor. In another example, the sensor 130 can be a Newtonian sensor, such as a gyroscope sensor, a vibration sensor, an accelerometer sensor, a three-dimensional (3D) accelerometer sensor, a force sensor, a pedometer, a strain gauge, and/or another Newtonian sensor.

In one example, the wearable stress-testing device 110, such as a wristband, can use the sensor array 120 to monitor a medical condition of an individual, such as a cardiac condition, under various environments or conditions for continuous, semi-continuous, or a periodic period of time on a long-term or protracted basis. In one example, sensor measurements can be collected using the sensor 130 in the sensor array 120 of the wearable stress-testing device 110. In one example, the sensor measurements can be stored on a non-tangible computer readable medium device 160 (e.g., a memory device) coupled to the wearable stress-testing device 110 or in communication with the wearable stress-testing device 110.

Figure 2:
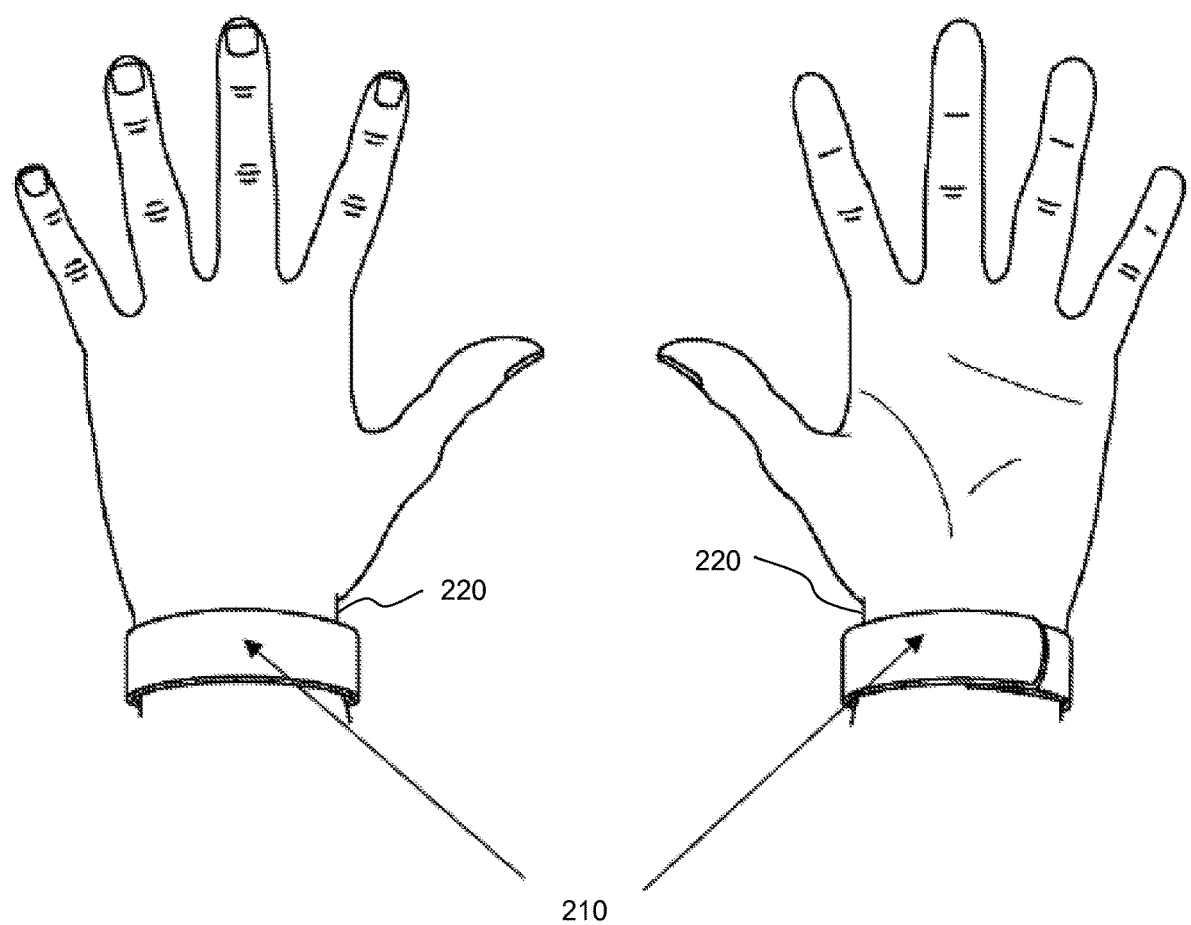
FIG. 2 depicts a top and a bottom perspective of a wearable stress-testing device attached to a wrist of an individual according to one embodiment.

FIG. 2 depicts a top and a bottom perspective of a wearable stress-testing device 210 attached to a wrist 220 of an individual according to one embodiment. The wearable stress-testing device 210 may be located on the wrist of an individual and may take one or more medical measurements at the wrist location. In one example, the wearable stress-testing device 210 can cover or wrap around the circumference of the wrist of the individual.

Figure 3:
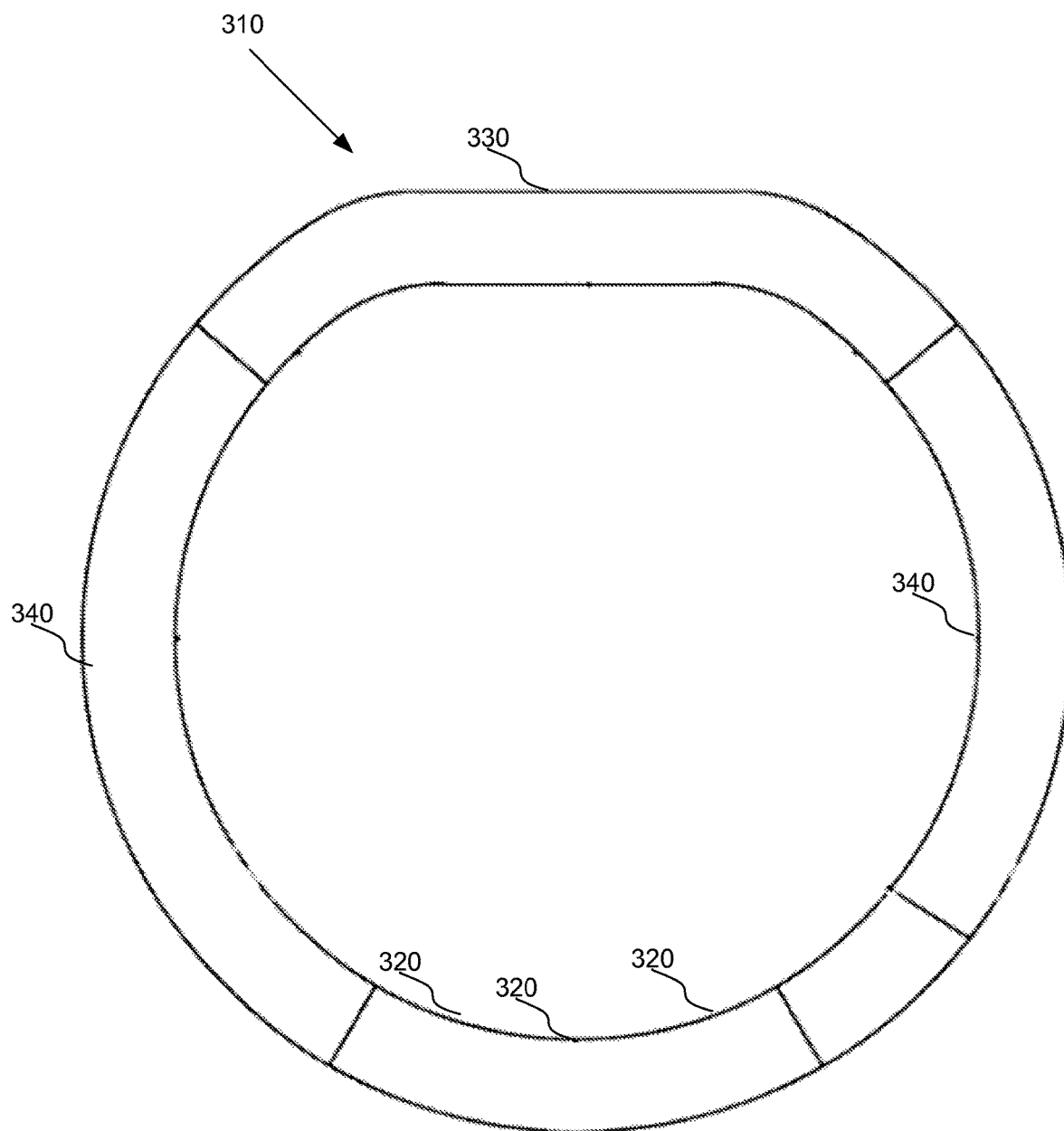
FIG. 3 depicts a side view of a wearable stress-testing device according to one embodiment.

FIG. 3 depicts a side view of a wearable stress-testing device 310 according to one embodiment. The wearable stress-testing device 310 may be the same as the wearable stress-testing device 210 as shown in FIG. 2. The wearable stress-testing device 310 can include one or more integrated sensors 320. In one exemplary embodiment, the wearable stress-testing device 310 can have a flat top portion 330 and a circular remaining portion 340 to fit to the contour or shape of a wrist on an individual. An advantage of the wearable stress-testing device 310 fitting to contours of the wrist can be to align the sensors 320 of the wearable stress-testing device 310 with a desired location on the wrist of the individual (such as a bottom, side, or top of the wrist). Another advantage of the wearable stress-testing device 310 fitting to contours of the wrist can be to provide and/or maintain proper contact between the sensor 320 of the wearable stress-testing device 310 and the body of the user. The location of the sensors 320 is not intended to be limiting. The sensor 320 can be located at different locations on the wearable stress-testing device 310. The shape of the wearable stress-testing device 310 is not intended to be limiting. The wearable stress-testing device 310 can be a variety of different shapes, such as oval, circular, rectangular, and so forth.

Figure 4:
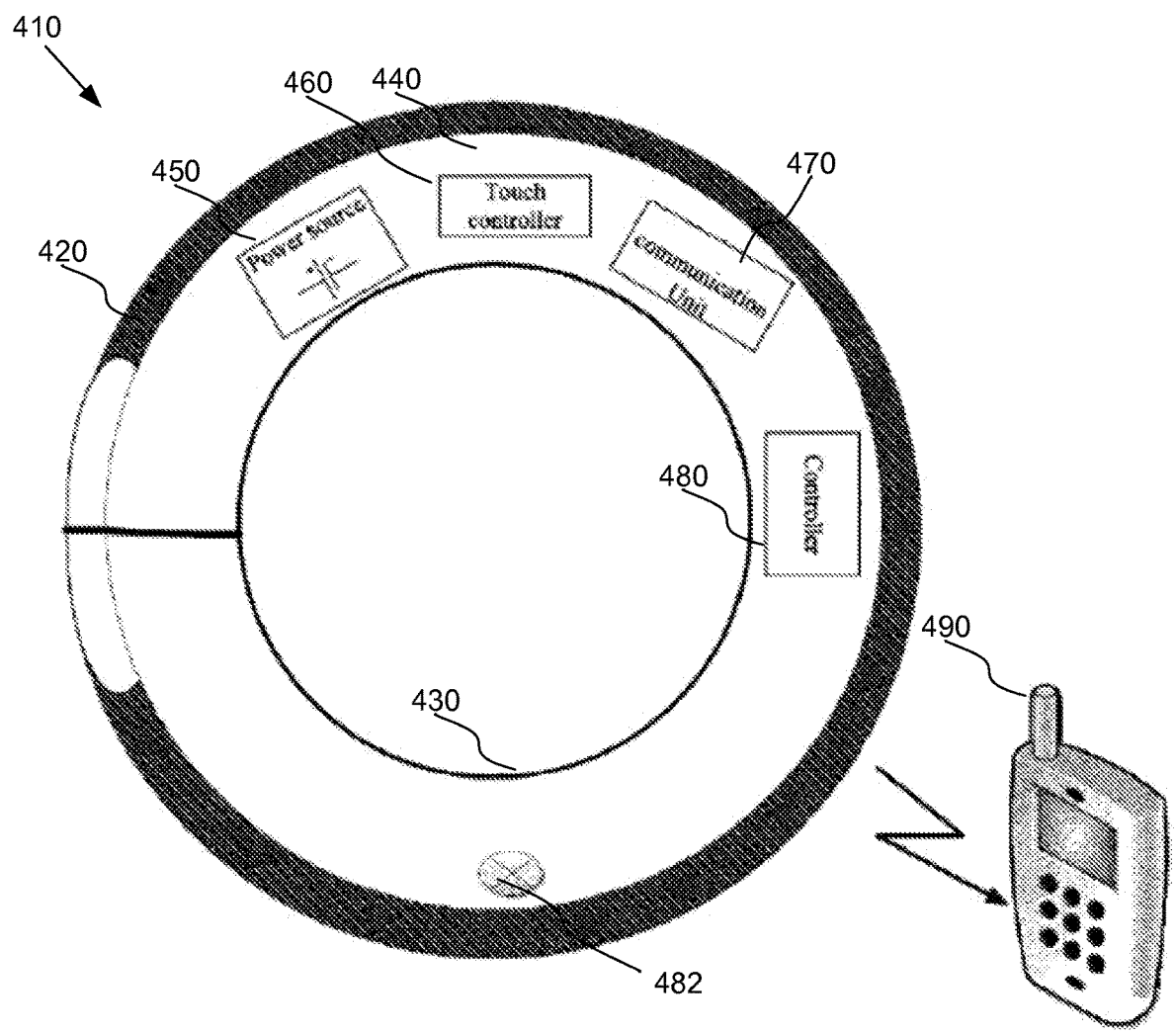
FIG. 4 depicts a wearable stress-testing device according to one embodiment.

FIG. 4 depicts a wearable stress-testing device 410 according to one embodiment. The wearable stress-testing device 410 can be a substantially circular band with an outer surface 420 and an inner surface 430. In one example, the outer surface 420 and an inner surface 430 can be made of flexible or non-rigid material, such as rubber, polyurethane, and so forth. In another example, the outer surface 420 and the inner surface 430 can be made of semi-rigid or rigid material, such as plastic, metal, and so forth. In one example, a cavity or chamber 440 can be between the outer surface 420 and an inner surface 430. The cavity or chamber 440 can include modules, units, systems, subsystems, or devices of the wearable stress-testing device 410. For example, a power source 450, a graphical user interface or touch controller 460, a communication unit 470, a controller 480, one or more sensors 482, and/or other units. In one example, the communication unit 470 can wirelessly communicate with an external electronic device 490. In another example, the power source 450 can provide power to other units or modules of the wearable stress-testing device 410. In one example the touch controller 460 can receive user input from an input device. In one example, the input device can be a graphical user interface (GUI) or a touch display and be operable to receive input via the GUI or the touch display. In another device, the input device can receive communications from other devices via a communication network (e.g., a wireless network) or a communication connection (such as a universal serial bus). In another example, the controller 480 can control systems and subsystems of the wearable stress-testing device 410.

In another example, the power source 450 can be a battery, such as a rechargeable battery. The power source 450 can receive power from another power source such as via a cord plugged into a power source or using wireless power such as inductive wireless charging or resonant wireless charging.

In one example, the wearable stress-testing device 410 receives health status information and/or health risk information of a user of the wearable stress-testing device 410. In one example the wearable stress-testing device 410 can have a touch controller 460 to receive user input health status information and/or health risk information. In one example, a power source 450, a touch controller 460, a communication unit 470, a controller 480, one or more sensors 482 can be in direct or indirect communication with each other. For example, the touch controller 460 receives user input information from the input device and communicates the user input information to the controller 480 and the controller 480 can have a computer processor to analyze or process the user input information. In another example, the sensor 482 can take a physiological measurement and communicate physiological measurement to the external electronic device 490 via the communication unit 470. In one example, the wearable stress-testing device 410 can have multiple sensors 482 (e.g., a sensor array). In one example, the plurality of sensors 482 can be different types of sensors.

Figure 5:
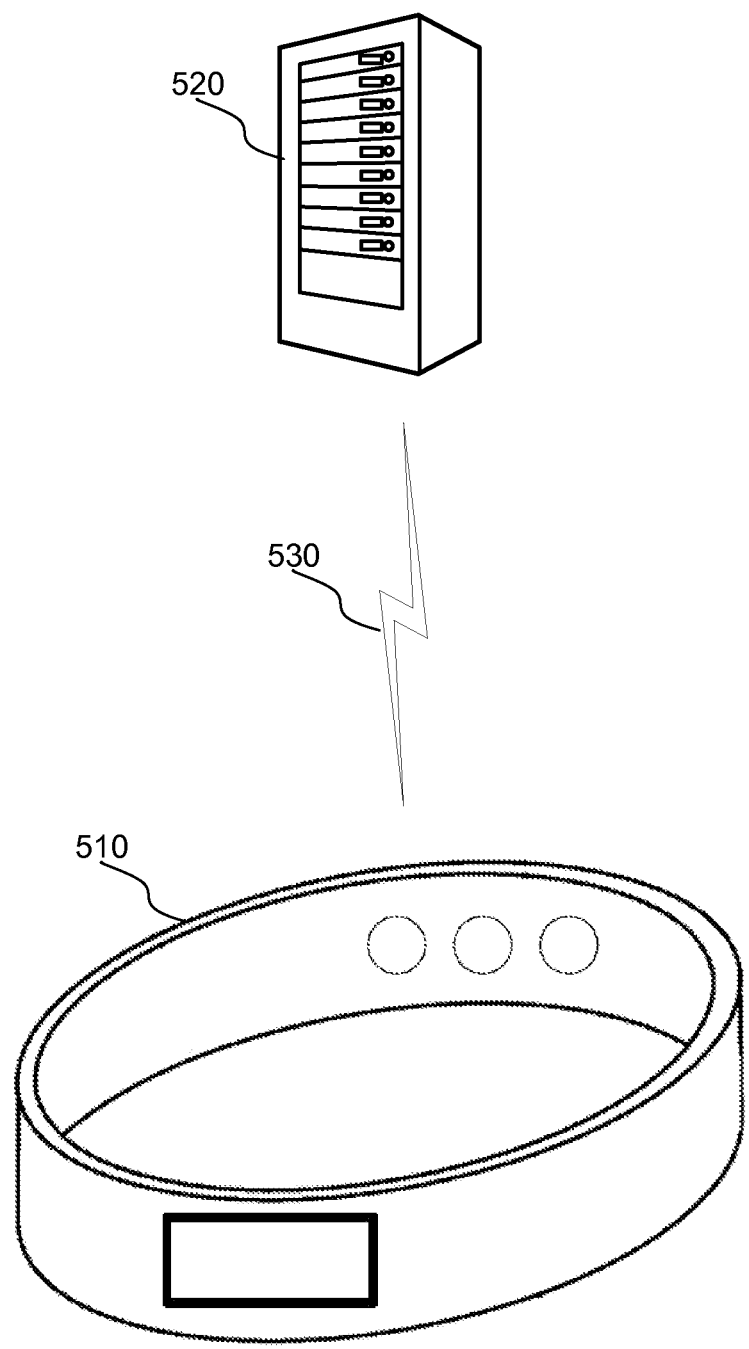
FIG. 5 depicts a wearable stress-testing device in direct communications with a computing device according to one embodiment.

FIG. 5 depicts a wearable stress-testing device 510 in direct communications with a computing device 520 according to one embodiment. In one example, the collected and/or stored sensor measurements can be processed or analyzed by a processor of the wearable stress-testing device 510 and/or by a computing device 520 in communication with the wearable stress-testing device. The wearable stress-testing device 510 can be in direct communication 530 with the computing device 520. In one example, the direct communication 530 can be a Bluetooth® communication link, a Zigbee® communication link, radio signal, or other direct communication systems. In one example, the other computing device 520 can be a server that stores information, such as physiological measurement information previously taken by the wearable stress-testing device 510 or physiological measurement information taken from a group of individuals, as discussed in the proceeding paragraphs. In another example, the other computing device 520 can be a mobile computer device, such as a laptop computer, tablet, or a smartphone. The wearable stress-testing device 510 can communicate information, such as physiological measurement information, to the other computing device 520. In one example, the other computing device 520 can process and/or analyze the measurements and/or data communicated from the wearable stress-testing device 510. In another example, the computing device 520 can communicate processed data, analyzed data, measurement results, and/or other information to the wearable stress-testing device 510. In another example, the computing device 520 can communicate calibration information to the wearable stress-testing device 510.

Figure 6:
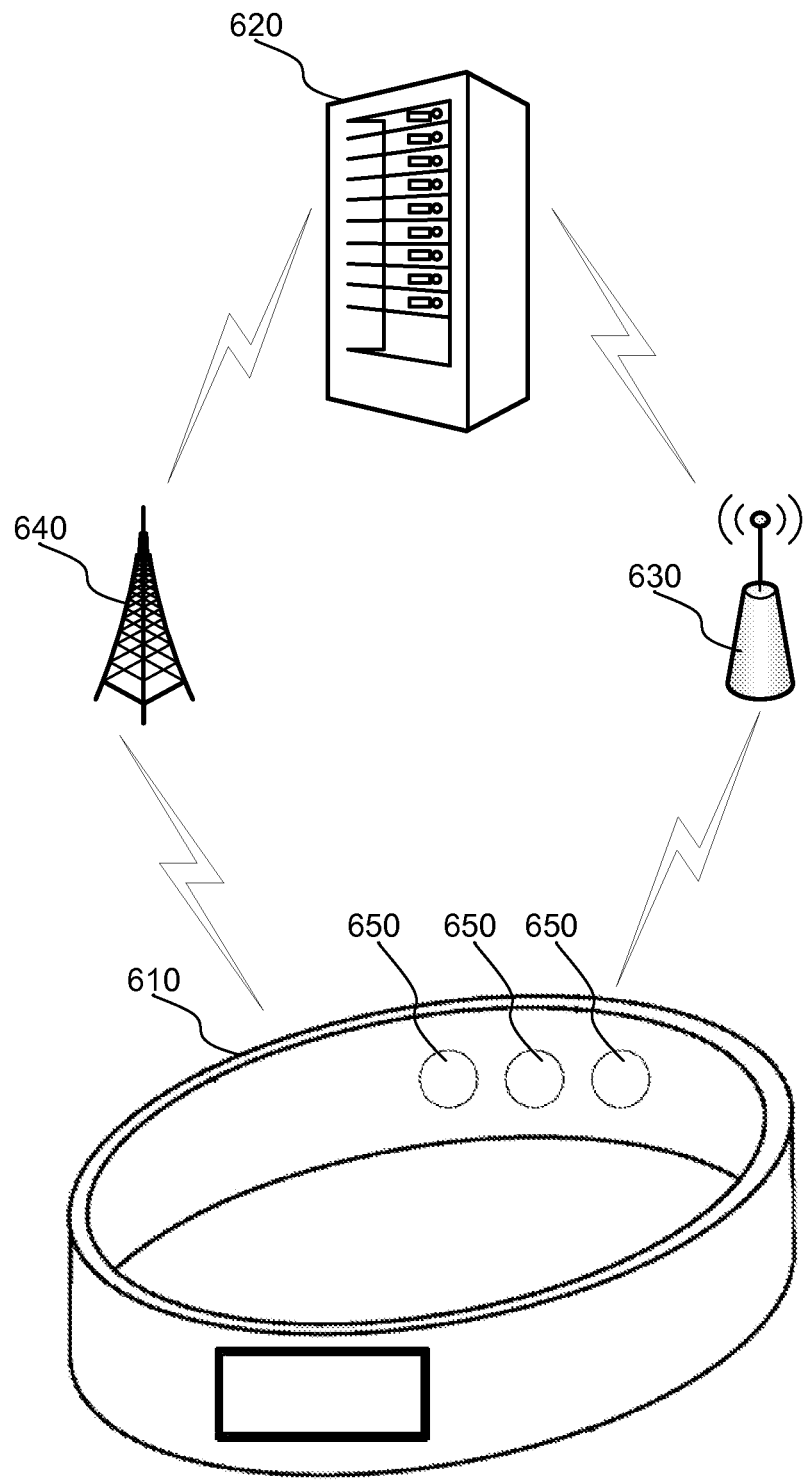
FIG. 6 depicts a wearable stress-testing device and a computing device in indirect communication using a communications network according to one embodiment.

FIG. 6 depicts a wearable stress-testing device 610 and a computing device 620 in indirect communication using a communications network according to one embodiment. The wearable stress-testing device 610 and the computing device 620 can be in indirect communication using a communications network such as wireless communication network 630 (such as a Wi-Fi® network) and/or using a cellular communication network 640 (such as a 3rd Generation Partnership Project (3GPP®) network) to communicate data or measurements. In one example, the wearable stress-testing device 610 can take physiological or medical measurements using a sensor 650 and communicate the physiological or medical measurements to the computing device 620 via the wireless communication network 630 and/or the cellular communication network 640. In another example, the computing device 620 can receive physiological or medical measurements from the wearable stress-testing device 610 via the wireless communication network 630 and/or the cellular communication network 640 and process the measurements and/or analyze the measurements. When the computing device 620 has processed the measurements and/or analyzed the measurements, the computing device 620 can communicate the processed measurements, analyzed measurements, measurement results, or other information to the wearable stress-testing device 610 via the wireless communication network 630 and/or the cellular communication network 640.

Figure 7:
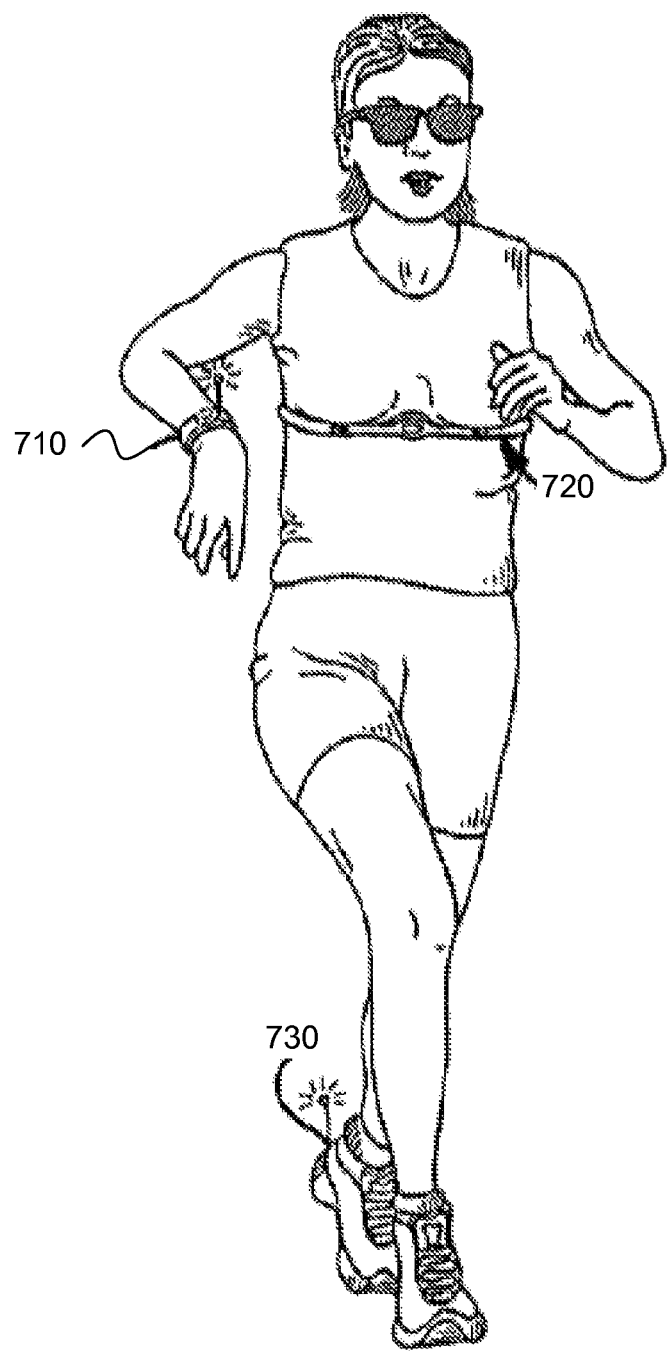
FIG. 7 depicts a wearable stress-testing device in communication with separate device according to one embodiment.

FIG. 7 depicts a wearable stress-testing device 710 in communication with a separate device 720 according to one embodiment. In another example, the wearable stress-testing device 710 can receive health status information and/or health risk information from the separate device 720. In one example, the separate device 720 can also be another wearable device. In one example, the separate device 720 can be a heart rate monitor worn around a chest of an individual. In one example, the wearable stress-testing device 710 and the separate device 720 can take medical measurements and the separate device 720 can communicate the medical measurement to the wearable stress-testing device 710 or vice versa. In one example, the separate device 720 can monitor a heart rate of an individual and communicate the heart rate information to the wearable stress-testing device 710. In another example, the wearable stress-testing device 710 can be in communication with a plurality of devices, such as separate devices 720 and 730. In one example, separate device 730 can be a movement sensor, such as an accelerometer that is attached to or built into a shoe.

Figure 8:
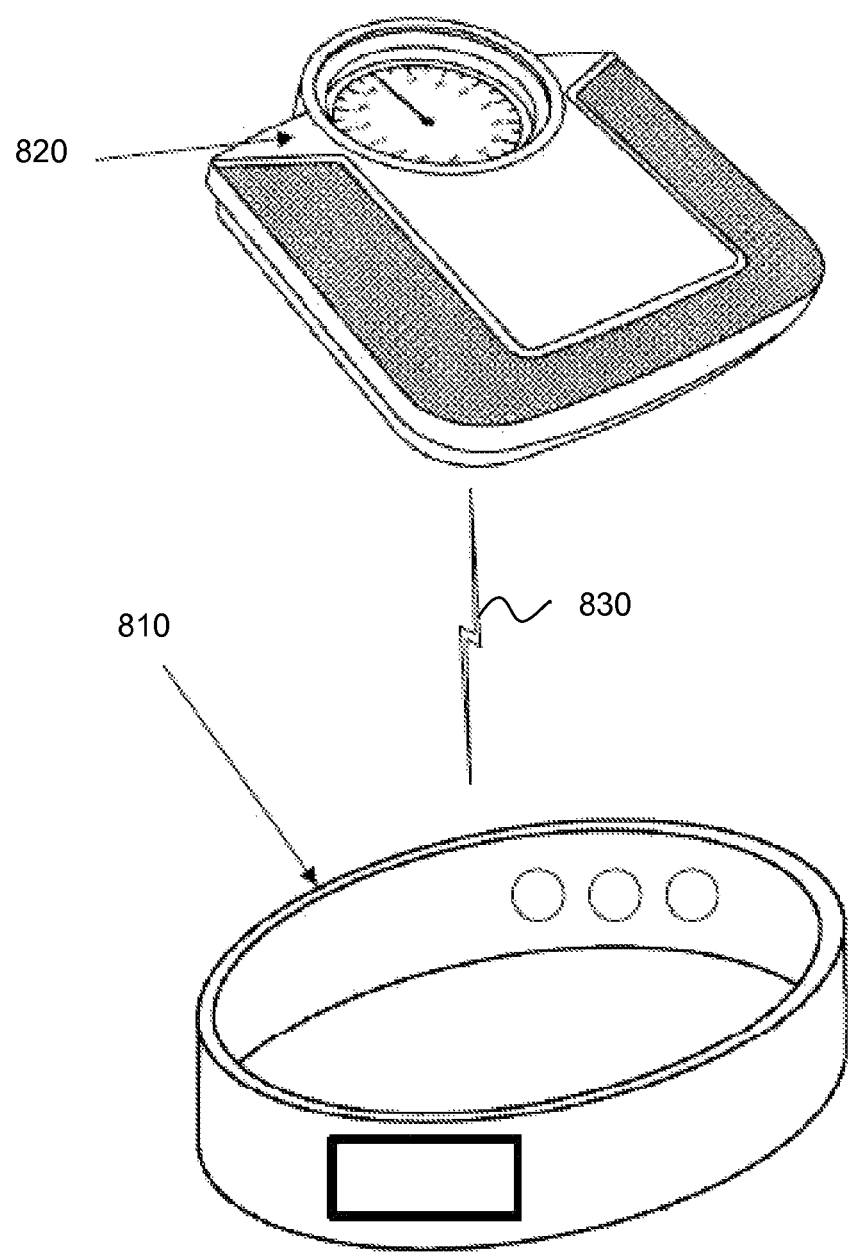
FIG. 8 depicts a wearable stress-testing device and a medical device according to one embodiment.

FIG. 8 depicts a wearable stress-testing device 810 and a medical device 820 according to one embodiment. The wearable stress-testing device 810 can be in communication with the medical device 820 using a communication network 830. In another example, the communications network 830 can be a cellular network that may be a 3GPP® LTE® Rel. 8, 9, 10, 11, or 12 or IEEE® 802.16p, 802.16n, 802.16m-2011, 802.16h-2010, 802.16j-2009, 802.16-2009. In another example, communications network 830 can be a wireless network (such as a wireless fidelity network (Wi-Fi®) that may follow a standard such as the Institute of Electronics and Electrical Engineers (IEEE®) 802.11-2012, IEEE® 802.llac, or IEEE® 802.llad standard. In another embodiment, the communications network 830 can be a Bluetooth® connection such as Bluetooth® v1.0, Bluetooth® v2.0, Bluetooth® v3.0, or Bluetooth® v4.0. In another example, the communications network 830 can be a Zigbee® connection such as IEEE® 802.15.4-2003 (Zigbee® 2003), IEEE® 802.15.4-2006 (Zigbee® 2006), IEEE® 802.15.4-2007 (Zigbee® Pro). In one example, the medical device 820 can be another wearable stress-testing device separate from the wearable stress-testing device 810. In another example, the medical device 820 can be a device unattached to the user.

Figure 9:
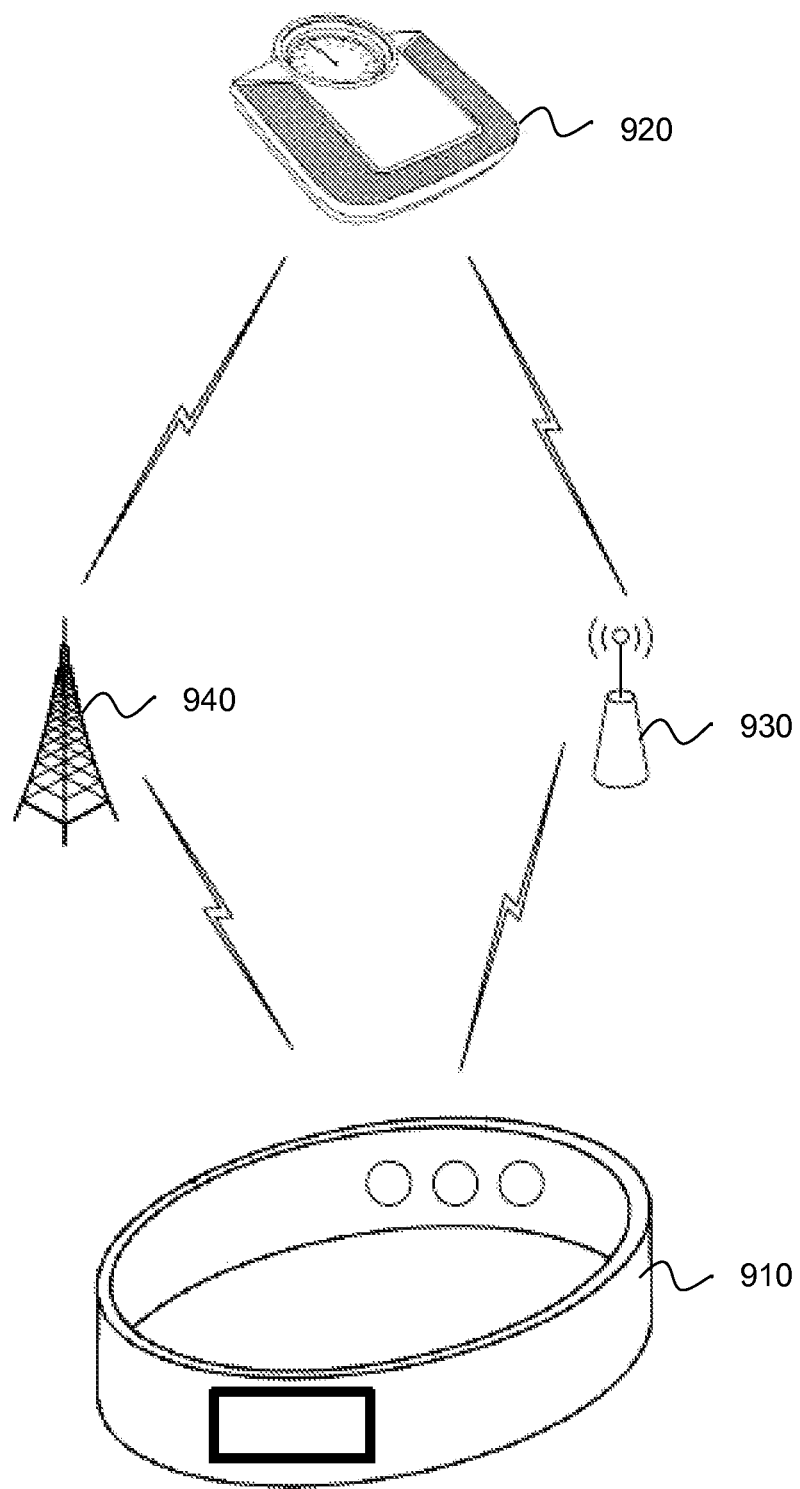
FIG. 9 depicts a wearable stress-testing device and a medical device in indirect communication using a communications network according to one embodiment.

FIG. 9 depicts a wearable stress-testing device 910 and a medical device 920 in indirect communication using a communications network according to one embodiment. The communications network can be a wireless communication network 930, such as a Wi-Fi® network, and/or using a cellular communication network 940, such as a 3GPP® network, to communicate data or measurements. In one example, the wearable stress-testing device 910 and/or the medical device 920 can take physiological or medical measurements. In one example, the wearable stress-testing device 910 can communicate the physiological or medical measurements to the medical device 920 using the communication network. In one example, the medical device 920 can communicate the physiological or medical measurements to the wearable stress-testing device 910 using the communication network. In one example, the wearable stress-testing device 910 and/or the medical device 920 can use the received physiological or medical measurements to calibrate one or more sensors or measurements of the wearable stress-testing device 910 or the medical device 920, respectively.

Figure 10:
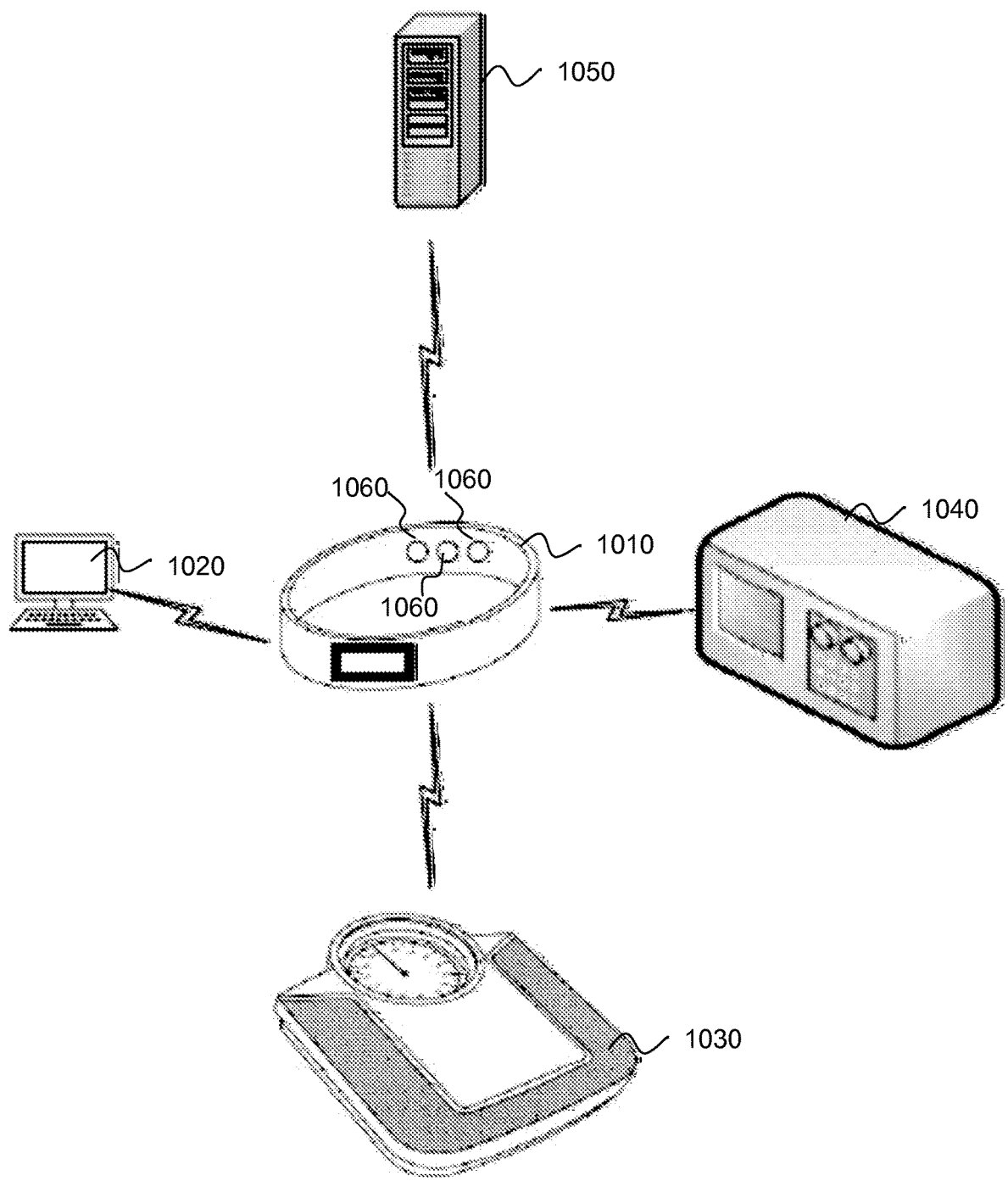
FIG. 10 depicts a wearable stress-testing device in communication with multiple devices according to one embodiment.

FIG. 10 depicts a wearable stress-testing device 1010 in communication with multiple devices according to one embodiment. The multiple devices can include a computing device 1020, a weight scale 1030, an electrocardiography (ECG) device 1040, and/or a server 1050. In one example, the wearable stress-testing device 1010 can receive medical or physiological measurements or data and/or user information from the one or more other devices 1020-1050. In one example, the wearable stress-testing device 1010 can uses the medical or physiological measurements or data and/or user information to calibrate the wearable stress-testing device 1010, one or more sensors 1060 of the wearable stress-testing device 1010, or measurements of the one or more sensors 1060 of the wearable stress-testing device 1010. In another example, the wearable stress-testing device 1010 can communicate medical or physiological measurements or data and/or user information to the one or more other devices 1020-1050. The types of multiple devices 1020, 1030, 1040, and 1050 described are not intended to be limiting, but rather provide examples of different types of devices in communication with the wearable stress-testing device 1010. Other types of devices can be in communication with the wearable stress-testing device 1010.

Figure 11:
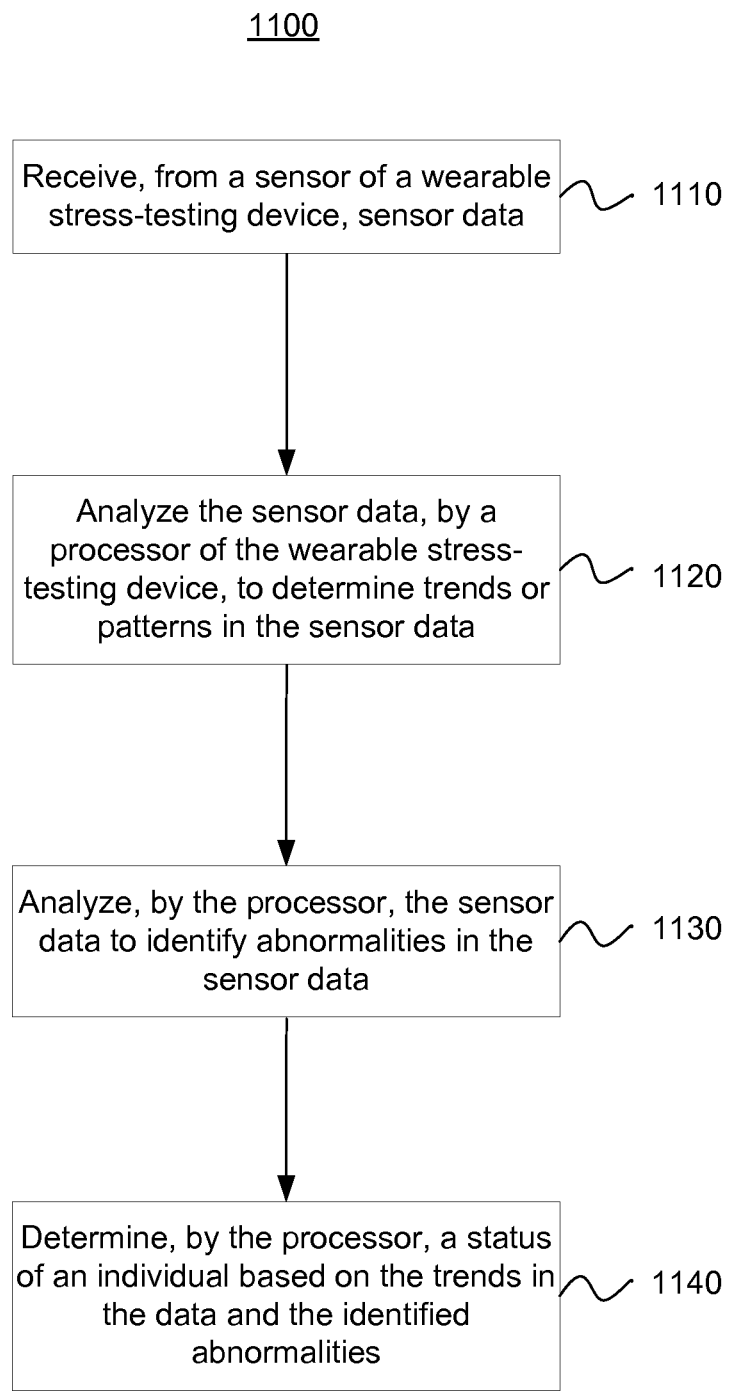
FIG. 11 depicts a flow diagram of a method for determining a status of an individual based on trends and/or abnormalities according to one embodiment.

FIG. 11 depicts a flow diagram of a method 1100 for determining a status of an individual based on trends and/or abnormalities according to one embodiment. Method 1100 may be performed by processing logic that may comprise hardware (e.g., circuitry, dedicated logic, programmable logic, microcode, etc.), software (such as operations being performed by the MCU), firmware or a combination thereof. In one example, method 1100 is performed by a processing device, a plurality of processing devices, a processor core, and/or a plurality of processor cores. Alternatively, other components of a computing system or software executing on the processing device may perform some or all of the operations of the method 1100.

Referring to FIG. 11, the method 1100 can begin by receiving, from a sensor of a wearable stress-testing device, sensor measurements (block 1110). In one example, the sensor measurements can be physiological measurements of a user, as discussed in the preceding paragraphs. In another example, the sensor measurements can be environmental measurements of an environment approximate the user. The method can include, analyzing the sensor measurements, by a processing device coupled to the wearable stress-testing device, to determine trends or patterns in the sensor measurements (block 1120). In one example, the sensor measurements can be analyzed to determine a consistent or recurring trending in the measurements for one or more conditions or situations when the individual is using the wearable stress-testing device. For example, when a user of the wearable stress-testing device exerts himself or herself, such as by climbing stairs or jogging, a heart rate of the user may increase while the oxygen saturation level of the user may decrease.

The method can further include, analyzing, by the processing device, the sensor measurements to identify abnormalities in the sensor measurements (block 1130). In one example, the wearable stress-testing device can compare current sensor measurements to previous measurements to determine abnormalities in the sensor measurements, for substantially similar exertions levels or other use conditions. For example, the wearable stress-testing device can analyze the sensor measurements to determine that historically when the individual exerts himself at a threshold exertion level, he has a heart rate or oxygen saturation level within a given range. The method can further include, updating, by the processing device, a status of the individual based on the trends in the measurements and/or the identified abnormalities (block 1140). For example, when the measurements may be trending in a positive direction (such as a reduction blood pressure or an increase in a hydration level), the status of the individual can be updated to indicate that the individual may be improving in health. In another example, when the measurements may be trending in a negative direction (such as an increase in blood pressure or a decrease in a hydration level), the status of the individual can be updated to indicate that the individual may be decrease in health. In another example, when the measurements may be trending in a positive direction (such as a reduction in blood pressure), a stress level of a bodily system can be updated to indicate a reduction of stress on the bodily system of the individual. In another example, when the measurements may be trending in a negative direction (such as a reduction in blood pressure), a stress level of a bodily system can be updated to indicate an increase of stress on the bodily system of the individual. In another example, when the measurements include an abnormality (such as a sudden spike in blood pressure or heart rate) the status of the individual can be updated to critical or needing assistance. In another example, when the measurements include an abnormality (such as a sudden spike in blood pressure or heart rate) the stress level of the individual can be updated to indicate an increase in stress on a bodily system of the individual. In this example, the stress level can be updated to indicate that the stress level may have reached a heart attack stress level or a stroke stress level. An advantage of a wearable stress-testing device that monitors an individual on a continuous, semi-continuous, or periodic basis can be to collect multiple measurement or data points for trend analysis. Multiple measurement or data points or measurement or data sets can be collected at different periods of time.

An analysis tool can be integrated into the wearable stress-testing device or coupled to the wearable stress-testing device. In one example, the analysis tool can be integrated or coupled to a cloud-based computing system that can communicate with the wearable stress-testing device. The analysis tool can determine a correlation between different measurement or data points or measurement or data sets of the input data (such as data collected from different sensors or devices). The analysis tool can determine different types of correlations of the measurement or data points or measurement or data sets. In one example, the analysis tool can use a Pearson product moment correlation coefficient algorithm to measures an extent to which two variables of input data may be related. In another example, the analysis tool can determine relations between variables of input data based on a similarity of rankings of different measurement or data points. In another example, the analysis tool can use a multiple regression algorithm to determine a correlation between a measurement or data set or a measurement or data point that may be defined as a dependent variable and one or more other measurement or data sets or other measurement or data points defined as independent variables. In another example, the analysis tool can determine a correlation between different categories or types of information in the input data.

In one example, when the analysis tool determines a correlation between the different measurement or data points or measurement or data sets, the analysis tool can use the correlation information to predict when a second event or condition may occur based on a first event or condition occurring. For example, the analysis tool can determine that a spike in blood pressure (e.g., the first event) may precede a heart attack (e.g., the second event). In another example, when the analysis tool determines a correlation between the different measurement or data points or measurement or data sets, the analysis tool can use the correlation information to determine a diagnosis or result data. In another example, when the analysis tool determines a correlation between the different measurement or data points and/or the measurement or data sets, the analysis tool can use the correlation information to determine a cause of a condition and/or event. For example, the analysis tool can determine, using an activity measurement, that a user of the wearable stress-testing device jogs for at least an hour. The wearable stress-testing device can monitor the blood pressure of the user during the hour-long jogs and when the user may not be jogging. In this example, the wearable stress-testing device can determine a correlation between jogging and the high blood pressure of the individual by determining that when the user may not be jogging that the blood pressure of the user is lower than when the user runs for at least an hour.

In one example, the analysis tool can determine a correlation between physiological measurements and environmental measurements. For example, the input measurements can include hydration level measurements (physiological measurements) and ambient temperature measurements (environmental measurements). In this example, the analysis tool may identify a correlation between when the ambient temperature increases and a decrease in a hydration level of a user. The analysis tool may identify the correlation between the ambient temperature and the hydration level by using a regression algorithm with the ambient temperature as an independent variable and the hydration level as a dependent variable. When the analysis tool has identified the correlation between the ambient temperature and the hydration level, the analysis tool can predict a change in a hydration level of a user or a rate of change of a hydration level of a user based on the ambient temperature.

In one example, the analysis tool can determine a correlation between physiological measurements and events, e.g., a time of day, a season of year, and so forth. In one example, the wearable stress-testing device can tag, or associate measurements taken using one or more sensors of the wearable stress-testing device with events, such as the time of the day, the season of the year, and so forth. For example, the wearable stress-testing device can tag measurements taken using the one or more sensors of the wearable stress-testing device with a time when an individual wakes up in the morning. In this example, the analysis tool may identify a correlation between when the user wakes up in the morning and an increased heart rate of the user. The analysis tool may identify the correlation between the event and the heart rate by using a regression algorithm with the event as an independent variable and the heart rate as a dependent variable. When the analysis tool has identified the correlation between the event and the heart rate, the analysis tool can predict a change in a heart rate of a user or a rate of change of a heart rate of a user based on the event. In another example, the analysis tool can determine a correlation between an altitude level and an oxygenation level of a user. For example, the analysis tool can determine a correlation between an increase in the altitude level and a decrease in the oxygenation level of the user. When the analysis tool determines the correlation between the altitude level and the oxygenation level, the analysis tool can predict a change in the oxygenation level of user based on the altitude level the user may be at. The preceding examples are intended for purposes of illustration and are not intended to be limiting. The analysis tool can identify a correlation between various measurement or data points, measurement, or data sets, and/or datatypes.

In one example, the analysis tool can identify a correlation between location information and physiological measurements of a user. For example, the analysis tool can determine a location of a user for a period of time, such as by using global positioning system (GPS) sensor measurements or triangulation sensor measurements. In this example, the analysis tool can receive physiological measurements (such as heart rate measurements, hydration level measurements, blood pressure measurements, and so forth). The analysis tool can correlate the location of the user with the physiological measurements to increase an accuracy of measurement analysis, a diagnosis, or result data and/or provide additional details regarding a cause of physiological measurements. [0056] In one example, the analysis tool can determine that a user is at work in an office location. When the analysis tool detects an increase in a heart rate or a blood pressure of a user, the analysis tool can correlate heart rate or blood pressure measurements with the location information to determine a cause of the increase in heart rate or blood pressure.

For example, when a heart rate or blood pressure of an individual increases while at a work in an office, the analysis tool may determine that the heart rate or blood pressure increase may be due to psychological causes (such as stress) rather than physiological causes (such as exercising or working out) because the user is at a location where an individual may be relatively less likely to physically exert himself or herself compared to an outdoor location or a gym location.

In one example, the analysis tool can use the multiple regression algorithm to determine a correlation between multiple physiological and/or environmental measurement or data points or measurement or data sets. For example, the analysis tool may receive heart rate measurements, skin temperature measurements, and hydration level measurements of a user. In this example, the analysis tool can determine a correlation between both a heart rate and skin temperature of an individual and a hydration level of the individual. For example, the analysis tool may determine that as the heart rate and the skin temperature of an individual increase, the hydration level of the individual may decrease.

In one example, the analysis tool can filter out a correlation determination (e.g., a determination that measurement or data points or measurement or data sets may be correlated) when the correlation level is below a threshold level. For example, when the analysis tool determines that there may be a thirty percent correlation between a skin temperature of an individual and a hydration level of an individual, the analysis tool may filter out the correlation information when determining a cause of a condition or event, a result of the measurements, or a diagnosis.

In another example, the analysis tool can discount or weight a correlation determination based on the correlation level of the correlation determination. For example, when the analysis tool determines that there may only be a thirty percent correlation between a skin temperature of an individual and a hydration level of an individual, the analysis tool may discount or assign a lower weight to the correlation determination (relative to a higher correlation percentage such as ninety percent) when determining a cause of a condition or event, a result of the measurements, or a diagnosis.

In one example, the analysis tool can assign weights to different factors, such as: physiological measurements, environmental measurements, time of day, and so forth. In one example, the analysis tool can assign a first weight to hydration level measurements of an individual and a second weight to heart rate measurements of an individual when determining a performance level of an individual, as discussed in the proceeding paragraphs. In this example, when determining a performance level, the analysis tool may assign a higher weight to the hydration level measurements relative to the heart rate measurements.

The analysis tool can use predetermined weights for the different physiological and/or environmental measurements. In one example, the analysis tool can receive user defined or predefined weights from an input device indicating the weights for the different physiological and/or environmental measurements. In another example, the analysis tool can determine the weights to assign to the different physiological and/or environmental measurements based on correlation levels of the different physiological and/or environmental measurements. For example, when a correlation level between a humidity level and a heart rate of an individual may be relatively low over a threshold period of time and/or under a threshold number of different conditions, the analysis tool may assign a low weight to humidity level measurements when determining a cause of a change in heart rate of a user.

In one example, the analysis tool can assign different weights to physiological measurements based on environmental measurements. For example, based on a location of an individual, the analysis tool can assign a first weight to a heart rate measurement and a second weight to a respiration sensor measurement. In another example, the analysis tool can assign weights to different causes, diagnosis, or results, such as: an exertion level (e.g., working out or sleeping), a stress level, an amount of time a user sleeps each day, and so forth.

In another example, the analysis tool can use environmental measurements to determine a cause of a physiological diagnosis. For example, when the user is located at a fitness facility, the analysis tool can increase a weight for physical exertion (e.g., working out) as a cause of physiological measurements (such as an increase in a heart rate or decrease in a hydration level of a user). In another example, when a user is located at home in bed, the analysis tool can correlate a location of the user with physiological measurements of the user. In this example, the analysis tool can determine that a decrease in heart rate may be due to an individual going to sleep when a user is located in their bedroom for a threshold period of time.

Figure 12:
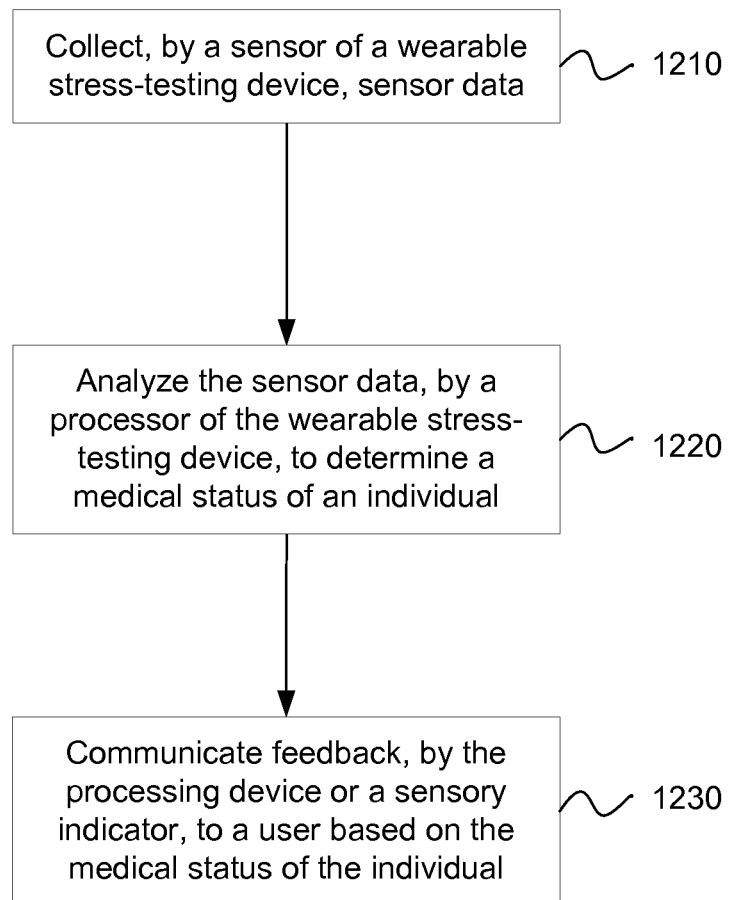
FIG. 12 depicts a flow diagram of a method for providing feedback based on a medical status of an individual according to one embodiment.

FIG. 12 depicts a flow diagram of a method 1200 for providing feedback based on a medical status of an individual according to one embodiment. Method 1200 may be performed by processing logic that may comprise hardware (e.g., circuitry, dedicated logic, programmable logic, microcode, etc.), software (such as operations being performed by the MCU), firmware or a combination thereof. In one example, method 1200 is performed by a processing device, a plurality of processing devices, a processor core, and/or a plurality of processor cores. Alternatively, other components of a computing system or software executing on the processing device may perform some or all of the operations of the method 1200.

Referring to FIG. 12, the method 1200 can begin by collecting, by a sensor of a wearable stress-testing device, sensor measurements (block 1210). The method can include analyzing the sensor measurements, by a processing device coupled to the wearable stress-testing device, to determine a medical status of an individual (block 1220). In one example, a medical status may include a predefined medical diagnosis of a good condition, a fair condition, a serious condition, a critical condition. In another example, the medical status may include a diagnosis of a cardiac infirmity such as tachycardia, bradycardia, and so forth. In another example, the sensor measurements may be analyzed, by a processing device, to diagnose a medical or physiological condition. In one example, the medical statuses can be set based on different threshold values for the sensor measurements. For example, when the sensor measurements may be for blood pressure, a first blood pressure threshold can be set for the good condition, a second blood pressure threshold can be set for the fair condition, a third blood pressure threshold can be set for the serious condition, and a fourth blood pressure threshold can be set for the critical condition. In this example, as the blood pressure measurement is below the first blood pressure threshold, the user may be in good condition; between the first blood pressure threshold and the second blood pressure threshold the user may be in fair condition; between the second blood pressure threshold and the third blood pressure threshold the user may be in serious condition; between the third blood pressure threshold and the fourth blood pressure threshold the user may be in critical condition.

In another example, the wearable stress-testing device can determine a trend in the sensor measurements, when the trend is increasing (e.g., a positive trend), the wearable stress-testing device can set an improving condition for the user. In another example, the wearable stress-testing device can determine a trend in the sensor measurements, when the trend is decreasing (e.g., a negative trend), the wearable stress-testing device can set a deteriorating condition for the user.

The method can further include communicating feedback, by the processing device or a sensory indicator, to a user based on the medical status of the individual (block 1230). In one example, the wearable stress-testing device can be configured to communicate feedback to a user or a third party, such as a caregiver or medical practitioner, for the medical status. In one example, the feedback can be communicated via a sensory indicator, such as a speaker (e.g., noise), a vibrator, and/or display (e.g., a graphical user interface) to communicate to the user or the third party the information. For example, when the wearable stress-testing device determines that the user may be having a heart attack, the wearable stress-testing device can communicate an auditory indication to the user to indicate to the user to call for help and/or to take medication. In another example, when the wearable stress-testing device determines that the user may be probable to have a medical condition, the wearable stress-testing device may indicate to the user to reduce or cease the current activity. For example, predetermined sensor measurements can be associated with medical conditions. For example, a blood pressure measurement exceeding 140 millimeters of mercury (mmHg) systolic can be associated with a medical condition of high blood pressure. When a user is performing an activity, such as jogging or climbing stairs, where the blood pressure measurement exceeds 140 mmHg, the wearable stress-testing device can indicate to the user to cease the jogging or stair climbing.

In one example, the computer circuitry can be configured to communicate activity adjustment indications. For example, the wearable stress-testing device can determine that the user of the wearable stress-testing device may have increased probability of fainting based on a blood pressure level and/or oxygen level of the user. When the wearable stress-testing device determines that the individual has an increased probability of fainting, the wearable stress-testing device can indicate to the user to decrease an activity exertion level or to cease a current activity, e.g., communicate a pre-event warning when a probability of an event occurring increases. In another example, the wearable stress-testing device can communicate feedback information when a measurement from one or more sensors in the sensor array of the wearable stress-testing device exceed a threshold or may be within a threshold range, such as a cardiac danger zone. In one example, the feedback can be an indication to decrease an activity exertion level or to cease a current activity. In one example, the computer circuitry can be configured to communicate feedback information to a user of the wearable stress-testing device, such as a patient, and/or a practitioner. One advantage of providing feedback to the user and/or the practitioner can be to use the feedback information in conjunction with diagnosis testing and/or medical treatment for a medical condition, such as a cardiac infirmity. Another advantage of providing feedback to the user and/or practitioner can be to determine which activities should be decreased or ceased.

In another example, the wearable stress-testing device can be adjusted to communicate training feedback for activities, such as military training activities or sports training activities. The wearable stress-testing device may determine that the user may be undertaking an activity based on a measurement from a sensor, user input defining the activity via a graphical user interface (GUI), a measurement from an accelerometer integrated into the wearable stress-testing device or other device, etc. For example, the wearable stress-testing device can be adjusted to communicate heart rate and breathing rate feedback for a sniper during shooting exercises. In this example, the wearable stress-testing device can determine that the sniper is performing shooting exercises by receiving user input via the GUI or by using a sensor to measure that the user may be attempting decrease their heart rate and breathing rate. In this example, the wearable stress-testing device can indicate to a user, such as a sniper, when the heart rate and breathing rate of the user has decreased below a threshold, e.g., indicating the user may be at a predefined physiological state to shoot a sniper rifle. The predefined physiological state may be one or more values, e.g., a heart rate value, a breathing rate value, a range of values input by the user, values determined from previous measurements of the user, values determined from crowdsourced data (as discussed in the proceeding paragraphs), and so forth.

In another example, the wearable stress-testing device can be adjusted to communicate training feedback to an athlete during athletic training. In one example, the wearable stress-testing device can indicate to a user, such as a swimmer or long-distance runner, that the heart rate and breathing rate may be within a predefined range for endurance training or athletic performance. The predefined range may also be input by the user, may be determined from previous measurements of the user, may be determined from crowdsourced data, and so forth.

Figure 13:
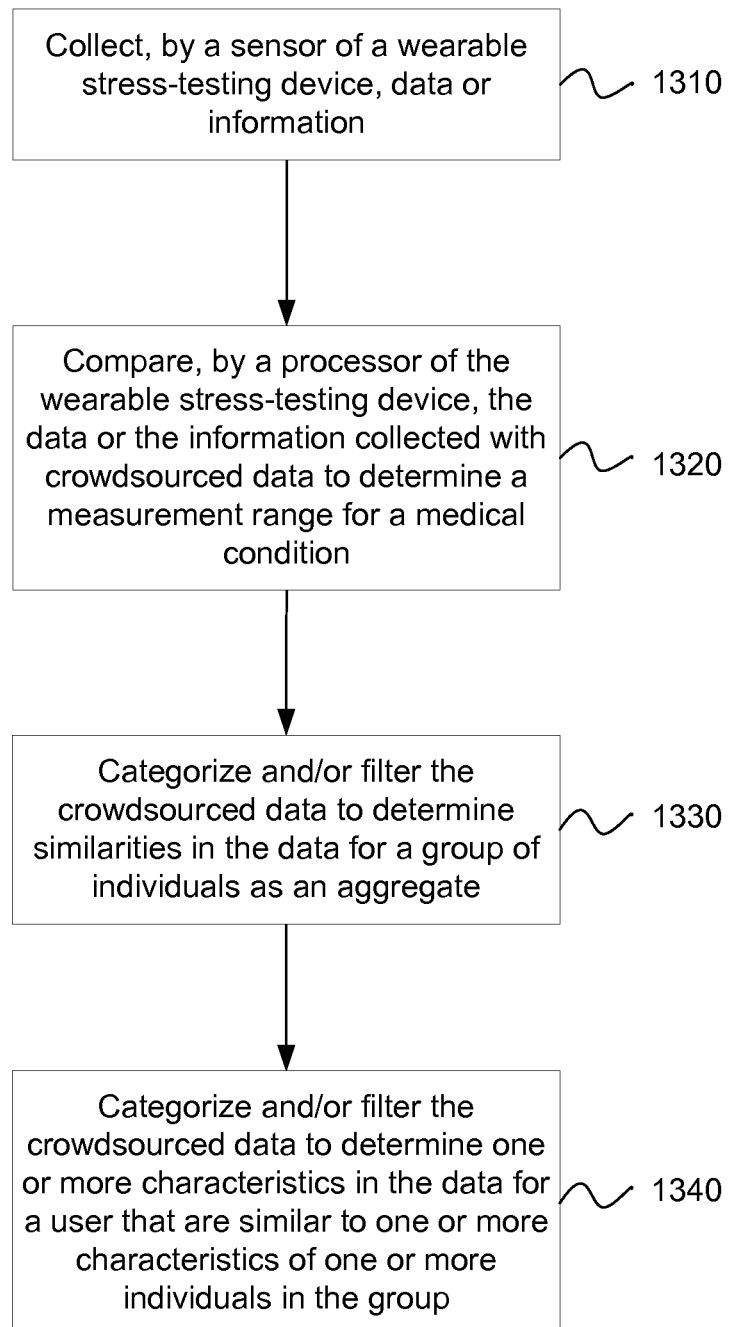
FIG. 13 depicts a flow diagram of a method for determining characteristics in measurements for a user that are similar to characteristics of individuals in a group according to one embodiment.

FIG. 13 depicts a flow diagram of a method 1300 for determining characteristics in data for a user that are similar to characteristics of individuals in a group according to one embodiment. Method 1300 may be performed by processing logic that may comprise hardware (e.g., circuitry, dedicated logic, programmable logic, microcode, etc.), software (such as operations being performed by the MCU), firmware or a combination thereof. In one example, method 1300 is performed by a processing device, a plurality of processing devices, a processor core, and/or a plurality of processor cores. Alternatively, other components of a computing system or software executing on the processing device may perform some or all of the operations of the method 1300.

Referring to FIG. 13, the method 1300 can begin by collecting, by a sensor of a wearable stress-testing device, data, or measurements (block 1310). The method can include, comparing, by a processing device coupled to the wearable stress-testing device, the data or the measurements collected with crowdsourced data, i.e., a measurement or data set or a measurement or measurement or data set collected from a group of individuals, to determine a measurement range for a medical condition (block 1320). The crowdsourced data may be stored on the wearable stress-testing device, may be stored on a server or cloud-based storage, and/or may be stored in another location. The method can include categorizing and/or filtering, by the processing device, the crowdsourced data to determine similarities in the data for the group of individuals as an aggregate (block 1330). For example, the crowdsourced data can be filtered to determine the range of measurements for the group of individuals for a medical measurement such as tachycardia with similar characteristics as the user of the wearable stress-testing device.

The method can include categorizing and/or filtering, by the processing device, the crowdsourced data to determine one or more characteristics in the data for a user that may be similar to one or more characteristics of one or more individuals in the group (block 1340). In another example, early cardiac event measurement patterns or pre-cardiac event measurement patterns can be a measurement or data set and/or measurement or data set collected from a group of individuals (crowdsourced data). In one example, the crowdsourced data can be categorized and/or filtered to determine similarities in the measurements for the group of individuals as an aggregate. For example, the crowdsourced data can be filtered to determine the range of measurements for the group of individuals for a cardiac event such as a heart attack. The method can further include comparing the categorized and/or filtered crowdsourced data with the measurements from the user to determine a medical status of the user.

In one example, the measurements for the individuals can be analyzed to determine trends in the measurements of the individuals, such as when the individuals may be at rest or exercising. The crowdsourced data can be categorized based on criteria, such as age, gender, weight, ethnicity, race, fitness level, geographical information, environmental, or other demographic criteria. In one example, the wearable stress-testing device can be calibrated based on the crowdsourced data by determining an average baseline measurement for the aggregated crowdsourced data and setting the baseline of the wearable stress-testing device at the average baseline calibration for the aggregated crowdsourced data.

In one example, a characteristic of the user of the wearable stress-testing device can be mapped to individuals in the group with similar characteristics. The baseline calibration of the individuals in the group can be as the baseline calibration for the user of the wearable stress-testing device. For example, a user can enter the demographic information of the user into the wearable stress-testing device and the wearable stress-testing device can map the user's entered demographic information to individuals with similar demographic information to determine expected ranges for medical measurements taken by the wearable stress-testing device. In one example, when a medical measurement or data may be outside a threshold range, the wearable stress-testing device can indicate to the user or a third party that the user may be experiencing a medical event.

Figure 14:
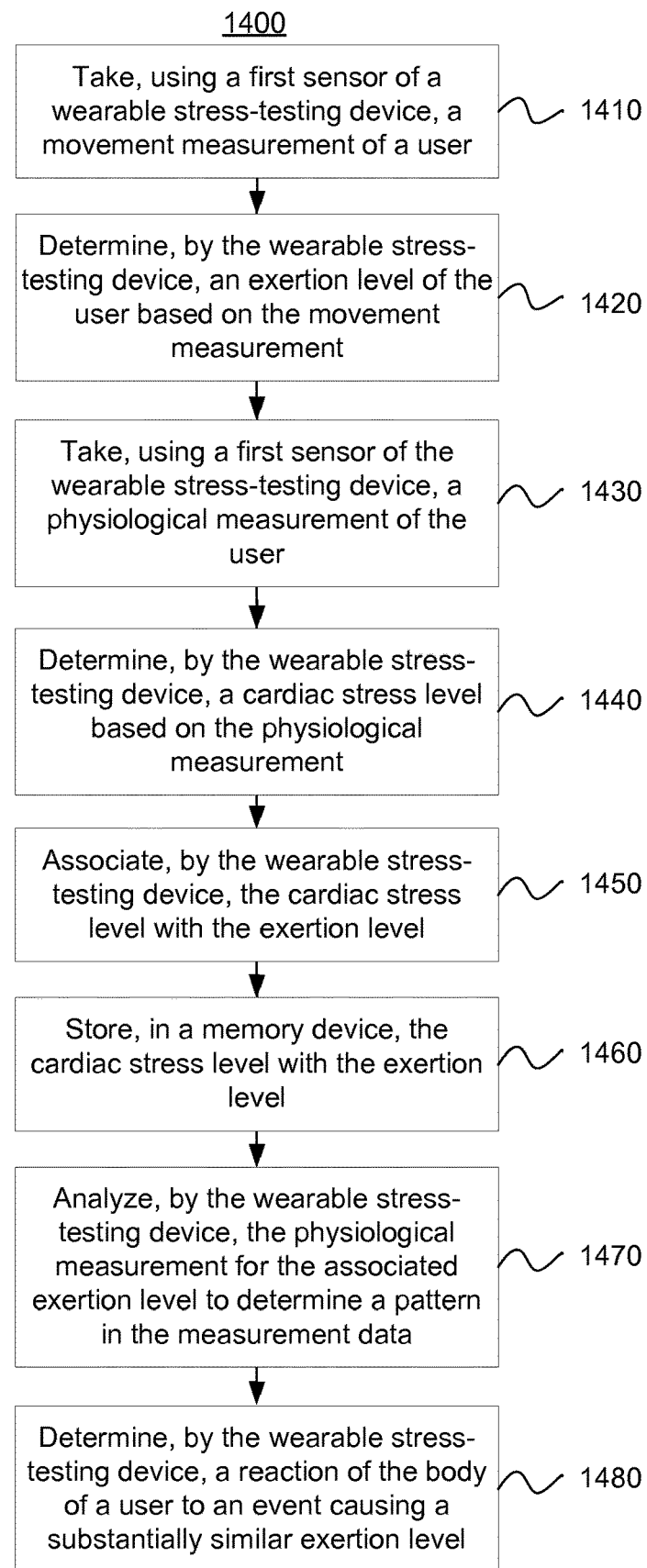
FIG. 14 depicts a flow diagram of a method for determining a reaction of a user to an event to one embodiment.

FIG. 14 depicts a flow diagram of a method 1400 for determining a reaction of a user to an event to one embodiment. Method 1400 may be performed by processing logic that may comprise hardware (e.g., circuitry, dedicated logic, programmable logic, microcode, etc.), software (such as operations being performed by the MCU), firmware or a combination thereof. In one example, method 1400 is performed by a processing device, a plurality of processing devices, a processor core, and/or a plurality of processor cores. Alternatively, other components of a computing system or software executing on the processing device may perform some or all of the operations of the method 1400.

[0076] Referring to FIG. 14, the method 1400 can begin by taking, using a first sensor of a wearable stress-testing device, a movement measurement of a user (block 1410). The method can include determining, by a processing device coupled to the wearable stress-testing device, an exertion level of the user based on the movement measurement (block 1420). For example, the processing device can receive a movement measurement from an accelerometer and determine that a movement of the user exceeds a threshold level associated with an exertion level. The method can include taking, using a first sensor of the wearable stress-testing device, a physiological measurement of the user (block 1430). The method can further include determining, by the processing device, a stress level (such as a cardiac stress level) based on the physiological measurement (block 1440). For example, the processing device can receive a measurement from a sensor associated with a cardiac bodily system of the user (such as a heart rate, blood pressure, or oxygenation level) and determine the stress level of the user based on predefined measurement levels for the cardiac bodily system. The method can include associating, by the processing device, the cardiac stress level with the exertion level (block 1450). In one example, the physiological measurement and/or the movement measurement can be non-invasive measurements, e.g., measurements that do not require physical penetration of the skin of the user, measurements taken by a sensor located outside of the body of the user, etc.

The method can further include storing, in a memory device, the cardiac stress level with the exertion level (block 1460). The method can further include, analyzing, by the processing device, the physiological measurement for the associated exertion level to determine a pattern in the measurements (block 1470). For example, when a user of the wearable stress-testing device exerts himself or herself at substantially the same exertion level and/or by performing substantially the same task, such as running a marathon, a heart of the individual can have a substantially similar reaction or response to the exertion. The method can further include determining, by the processing device, a reaction of the body of a user to an event causing a substantially similar exertion level (block 1480).

In one example, the wearable stress-testing device can indicate the determined reaction to the user. In another example, the wearable stress-testing device can iteratively analyze physiological measurement for events causing different exertion levels. For example, the wearable stress-testing device can collect stress measurements for different exertion events including when the user may be sleeping, waking up, driving to work, climbing stairs, jogging, watching television, and so forth. The wearable stress-testing device analyzes the stress measurements for the different exertion events to determine a pattern of how the body of the user reacts to different kinds of exertion events and/or different levels of exertion. One advantage of using the wearable stress-testing device to collect cardiac stress information can be to enable the user to collect the cardiac stress information without overly straining the cardiac system of the user. For example, rather than the stressing the cardiac system of an individual by running on a treadmill at speeds or inclines that exceed an exertion that the individual may be accustomed to, the wearable stress-testing device can enable monitoring of the individual in a normal environment of the individual and/or at a normal exertion level of the individual. The individual can continuously use the wearable stress-testing device during regular activities and collect cardiac stress information. The wearable stress-testing device can provide a safer procedure for collection of cardiac stress information by enabling cardiac stress monitoring in the normal environment of the individual rather than artificially induced cardiac stress environments or cardiac stress situation to which the individual may not be accustomed.

The wearable stress-testing device can increase the accuracy of cardiac stress measurements. Normally, a doctor can administer a cardiac stress test for a period of time, such as one to two hours. The traditional cardiac stress test can have limited accuracy, as a cardiac event may not occur during the select period of time and/or under the exertion event. The wearable stress-testing device can take cardiac stress measurements during a wider variety of user activities and/or for an extended period of time. The increased scope of activities during which cardiac stress can be measured and the extended period of time during which cardiac stress measurement can be taken can increase the accuracy of the cardiac stress measurement by providing an increased number of measurement or data points for a large number of activities.

Figure 15:
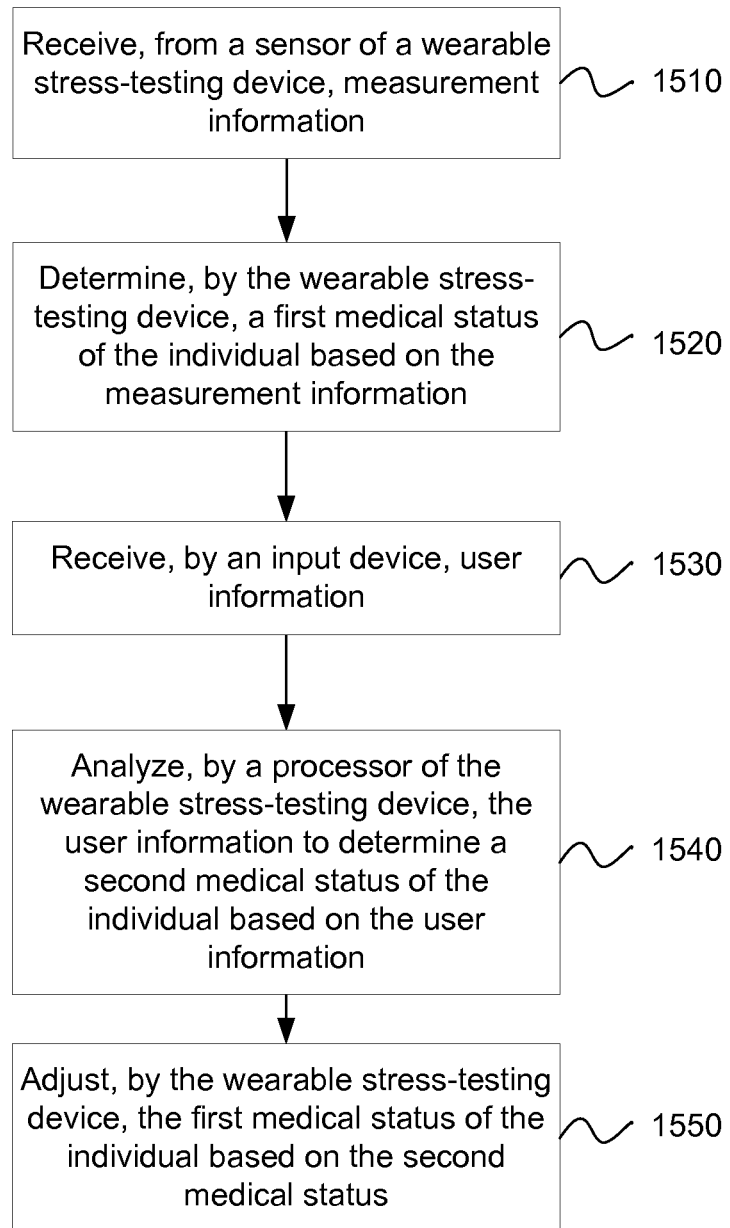
FIG. 15 depicts a flow diagram of a method for adjusting a medical status of a user according to one embodiment.

FIG. 15 depicts a flow diagram of a method 1500 for adjusting a medical status of a user according to one embodiment. Method 1500 may be performed by processing logic that may comprise hardware (e.g., circuitry, dedicated logic, programmable logic, microcode, etc.), software (such as operations being performed by the MCU), firmware or a combination thereof. In one example, method 1500 is performed by a processing device, a plurality of processing devices, a processor core, and/or a plurality of processor cores. Alternatively, other components of a computing system or software executing on the processing device may perform some or all of the operations of the method 1500.

Referring to FIG. 15, the method 1500 can begin by receiving, from a sensor of a wearable stress-testing device, measurement information (block 1510). The method can further include determining, by a processing device coupled to the wearable stress-testing device, a first medical status of the individual based on the measurement information (block 1520). The method can further include receiving, by an input device, user information (block 1530). In one example, the input device can be a GUI or a touch screen display of the wearable stress-testing device. In another example, the input device can receive user information from another device. The method can include analyzing, by the processing device, the user information to determine a second medical status of the individual based on the user information (block 1540). The method can include adjusting, by the processing device, the first medical status of the user based on the second medical status (block 1550). In one example, the received user information may include: a user age; a user physical ability, such as ability to perform a particular task (e.g., run one mile, walk one mile, swim 500 meters), a range of motion, and so forth; a user health level or status; user risk information; environmental conditions; or a user psychological condition, such as anxiety, nervousness, agitation, depression, elation, and so forth. In one example, analyzing the received user information may comprise comparing the received user information to at least one of past user data, crowdsourced data, concurrent physiological data of the user, or other information.

Normally, the use of cardiac stress testing for elderly individuals has been limited. For example, elderly individuals may suffer from illnesses, such as pneumonia, that limit the amount of energy the elderly individual can exert for a traditional stress test. In another example, elderly individuals can suffer from physical limitations such as arthritis or bad joints that limit the range of motion and exertion levels of the elderly individual during a traditional stress test. In one example, the wearable stress-testing device can be adjusted based on the age and/or physical ability of the user of the wearable stress-testing device. For example, the wearable stress-testing device can receive age and/or physical ability level information from the user, such as via a graphical user interface or via a wireless communication with another device. The wearable stress-testing device can adjust the measurement analysis and/or feedback level based on the received age and/or physical ability level information of the user. In one example, a received age can be an age that exceeds a senior citizen age (e.g., above 65 years old). In this example, the wearable stress-testing device can adjust a measurement analysis of the likely activities the senior citizen user may perform (such as the senior citizen user may not be likely to run marathons). One advantage of a wearable stress-testing device can be that the wearable stress-testing device can continuously monitor an individual, such as an elderly individual, during a range of activities that may not be tested during a traditional stress test, such as running on a treadmill or riding an exercise bike. The wearable stress-testing device can gather or collect stress-testing measurements for individuals that may not be physically capable of doing a traditional stress test. Another advantage can be that the wearable stress-testing device can be adjusted based on the physical limitations and physical ability level of the user to account for the limited range of activities the individual can perform.

In one example, the wearable stress-testing device can adjust cardiac stress measurements taken by one or more sensors of the wearable stress-testing device based on the health status information and/or health risk information. For example, when the health risk information of a user of the wearable stress-testing device indicates that the user has a higher-than-average cardiac health risk, such as a high risk of stroke or heart attack, the wearable stress-testing device can increase a sensitivity of a sensor in a sensor array. For example, the wearable stress-testing device can receive user information via an input device indicating a high cardiac health risk of the user. In this example, the wearable stress-testing device can increase a sensitivity of the sensor because of the high cardiac health risk of the user. In another example, the user can manually adjust a sensitivity of the sensor (e.g., increase or decrease the sensitivity). For example, a user may desire to have finer detailed measurements and can adjust sensitivity of the sensor to capture the finer detail.

In another example, the wearable stress-testing device can use a different data analysis scrutiny level, including: a high data scrutiny level, a normal data scrutiny level, and a low data scrutiny level. In one example, the normal data scrutiny level can be a baseline scrutiny level, the high data scrutiny level can be a scrutiny level at a predefined level above the baseline scrutiny level, and the high data scrutiny level can be a scrutiny level at a predefined level below the baseline scrutiny level. For example, when the health risk information of a user of the wearable stress-testing device indicates that the user has a higher-than-average cardiac health risk, the wearable stress-testing device can switch from a normal data scrutiny level to a high data scrutiny level, where the wearable stress-testing device can increase a data analysis depth level of measurements from the sensors. In another example, when the health status information of a user of the wearable stress-testing device indicates that the user may be sick or ill, the wearable stress-testing device can switch from a normal data scrutiny level to a low data scrutiny level, where the wearable stress-testing device can decrease data analysis depth level of measurements from the sensors to account for the effect of the sickness or illness on the measurement data. In another example, when the wearable stress-testing device may be operating in at a normal data scrutiny level, the wearable stress-testing device may alert the user or a medical professional when the measurements deviate from a baseline by a first threshold value. When the data analysis scrutiny level may be switched to a high data scrutiny level, the user or the medical professional may be alerted when the measurements deviate from the baseline by a second threshold value. In one example, the second threshold value may be less than the first threshold value. When the data analysis scrutiny level may be switched to a low data scrutiny level, the user or the medical professional may be alerted when the measurements deviate from the baseline by third threshold value. In one example, the third threshold value may be greater than the first threshold value.

In one example, analysis of the measurements can be adjusted based on the health level of the individual. For example, an elderly individual can have an increased susceptibility to the flu. Under normal health conditions the elderly individual may not present any measurements indicating a cardiac condition except for when the health level of the elderly individual decreases, e.g., when they may be in a weakened condition and more susceptible to a cardiac event. The wearable stress-testing device can adjust the sensors of the wearable stress-testing device and/or the data analysis based on the health level of the individual, such as increase in a sensitivity level of the data analysis when the individual may be ill.

In another example, the wearable stress-testing device can adjust the sensors of the wearable stress-testing device and/or the measurements based on environmental conditions of the area where a user is located. In one example, the environmental conditions or environmental measurements can include: altitude, air quality, temperature, humidity, weather, ambient noise level, road-rage, and so forth. In one example, the wearable stress-testing device can detect when the air quality of a user environment is below average or below a threshold value and adjust the wearable stress-testing device to account for the increased stress on a cardiovascular system of a user based on the bad air quality.

In another example, the wearable stress-testing device can adjust the sensors of the wearable stress-testing device and/or the measurements based on a psychological condition of the user. A psychological condition can include: a mood of a user, anxiety level, stress level, sleep level, and so forth. In one example, the wearable stress-testing device can measure the psychological condition of the user based on the cardiac reaction of a user when no physical exertion occurs or when minimal physical exertion occurs. For example, the wearable stress-testing device can detect an increased anxiety level when a user of the wearable stress-testing device may not physically be exerted himself and the heart rate and breathing rate of the user increased beyond a threshold. In another example, the wearable stress-testing device can detect the psychological condition by analyzing the measurements to determine a trembling or jittering level of an individual, a body temperature level of an individual, a sweat rate of an individual, a blood pressure of an individual, and so forth. In another example, the wearable stress-testing device can use a graphical user interface to receive psychological condition information from the user. In another example, the wearable stress-testing device can receive psychological condition information from another device.

In one example, the wearable stress-testing device can monitor the cardiac stress of an individual at different times of a day and/or during different activities. For example, the wearable stress-testing device can monitor the cardiac stress of an individual when the individual is sleeping, when the individual wakes up in the morning, when the individual is at work, when the individual exerts himself or exercises, when the individual engages in sexual activity, and other select periods. An advantage of the wearable stress-testing device may be that in addition to providing diagnostic information, the wearable stress-testing device can monitor a patient on an ongoing basis under a wider variety of conditions such as the time of day and variations in emotional, physical, and mental states.

In another example, the wearable stress-testing device can monitor the cardiac stress of an individual during periods or activities that increase a risk of the individual suffering from a cardiac episode. For example, the body of an individual has a circadian rhythm (i.e., a biological clock) that can increase or decrease the risk of a cardiac episode occurring during certain hours or activities. In one example, an individual can be at an increased risk of a cardiac episode, such as a heart attack or stroke, when the individual wakes up in the morning. For example, the body of an individual demands an increased oxygen supply to support a number of bodily functions during a period of time after the individual wakes up. As the individual wakes up and starts his daily physical activities, his systolic blood pressure and heart rate can have the largest upward increase in early hours of the morning relative to the rest of the day. Additionally, the ability of blood vessels to dilate in response to increased blood flow can be compromised, blood clots can be more likely to form, and the ability of the body of the individual to break the blood clots up can be at its lowest point during the morning. The increased systolic blood pressure and heart rate as well as the compromised ability of blood vessels to dilate can cause an increase in demand for oxygen and contribute to the constriction of blood vessels. Additionally, an increase in blood clots can contribute to the reduction of blood flow or even blockage of the blood vessels heading to the heart.

The wearable stress-testing device can store predetermined cardiac stress patterns for periods of a day and compare cardiac stress measurements of the user for the predetermined patterns to determine when the user has an increased probability of having a cardiac event. For example, the wearable stress-testing device can have one or more predetermined cardiac stress patterns for the morning based on the usual cardiac stress on the body of a user as discussed in the preceding paragraphs. The wearable stress-testing device can compare the current cardiac stress measurements of the user with the predetermined cardiac stress patterns to determine when the current measurements indicate a similar pattern to the predetermined cardiac stress patterns. In one example, the predetermined cardiac stress patterns can be patterns for an increased probability of a user having a stroke or heart attack. When the wearable stress-testing device determines that the user has similar cardiac stress patterns, the wearable stress-testing device can alert the user and/or a third party.

In one example, the wearable stress-testing device can receive medical regimen information, such as a doctor's recommendation to walk a distance per day, and the wearable stress-testing device can correlate or pair cardiac activities with the medical regimen information. The medical regimen information may be received by input on a touch screen, by input on a GUI, from another device, by accessing a server, and so forth. In one example, a doctor can recommend that an individual walk four miles per day to decrease the blood pressure level of the individual and to decrease a risk of a cardiac activity. In this example, the wearable stress-testing device can receive the regimen information of walking four miles per day and correlate measurements with the cardiac activity during the period the individual is walking the four miles. In one example, the wearable stress-testing device can receive a regimen engagement message, such as receiving the regimen engagement message using a graphical user interface or a user pushing a button of the wearable stress-testing device, indicating that the individual is starting or stopping the regimented activity. In another example, the wearable stress-testing device can receive a regimen engagement message from another device.

In one example, an individual may not be aware of a cardiac condition until a severe cardiac event, such as a heart attack, occurs. In one example, several mild cardiac events can go undetected until a cardiac condition of an individual worsens. In one example, the wearable stress-testing device communicates an early warning indicator to a user to signal that the wearable stress-testing device received measurements from one or more of the sensors of the wearable stress-testing device showing early cardiac event measurement patterns or pre-cardiac event measurement patterns. In one example, the wearable stress-testing device can store early cardiac event measurement patterns or pre-cardiac event measurement patterns and compare the measurements of the user with the stored measurements.

The wearable stress-testing device can detect repetitive patterns in the cardiac measurements and can calibrate the wearable stress-testing device to filter out the repetitive patterns. In one example, the wearable stress-testing device can alert the user and/or a third party of repetitive patterns in the cardiac measurements. For example, when the user of the wearable stress-testing device has previously had a cardiac episode as the user wakes up in the morning or exercises at intense levels, the wearable stress-testing device can determine that another cardiac episode may be probable to occur (e.g., above a threshold probability level based on past or historical occurrences) and can alert or indicate to the user and/or the third party when a cardiac episode may be likely to happen (e.g., indicate a time of day or activity level during which the user has had cardiac episodes and during which the user may continue to have cardiac episodes, etc.).

In another example, the wearable stress-testing device can monitor long-term trends in the measurements. For example, the wearable stress-testing device can monitor the long-term effects of exercise on the body of the user. In one example, the wearable stress-testing device can monitor long-term effects of exercise by monitoring a decrease in blood pressure, a decrease in breathing rate during exercise compared to a breathing rate during a period before the user regularly exercised, a decrease in the exertion level of a cardiac system of the user during an exertion period compared to a period before the user regularly exercised, and so forth. In another example, the wearable stress-testing device can measure negative effects on the body of an individual. For example, the wearable stress-testing device can monitor the short-term and/or long-term effects on the body of an individual when the individual smokes cigarettes. In one example, the wearable stress-testing device can monitor a short-term cardiac endurance level of an individual for a period of time when the individual does not smoke cigarettes and a period of time when the individual smokes cigarettes. In another example, the wearable stress-testing device can monitor a long-term cardiac endurance level of an individual as the individual begins to smoke cigarettes or smokes cigarettes for an extended period of time. In another example, the wearable stress-testing device can monitor a change in a physiological change of the body of an individual, such as a change in the cardiac system, based on a change of habit of the individual. For example, the wearable stress-testing device can receive nutritional or dietary information, such as by using a graphical user interface (GUI) or from another device, and the wearable stress-testing device can monitor a physiological change of the body of an individual based on a change in the nutritional or dietary information of the individual.

In another example, the wearable stress-testing device can be adjusted to detect and/or analyze sensor measurements (such as cardiac measurements) for cardiac events. For example, the wearable stress-testing device can be adjusted to analyze the cardiac measurements for tachycardia, i.e., a heart beating irregularly fast. In another example, the wearable stress-testing device can be adjusted to detect biological arrhythmias, such as heart arrhythmias. One advantage of detecting and/or analyzing cardiac measurements for cardiac events can be to customize the wearable stress-testing device to monitor for select medical conditions or medical risks. For example, the wearable stress-testing device can be customized for an individual with an increased risk of a stroke by adjusted the wearable stress-testing device to monitor for a cardiac arrhythmia, which can be a precursor of a stroke.

Figure 16:
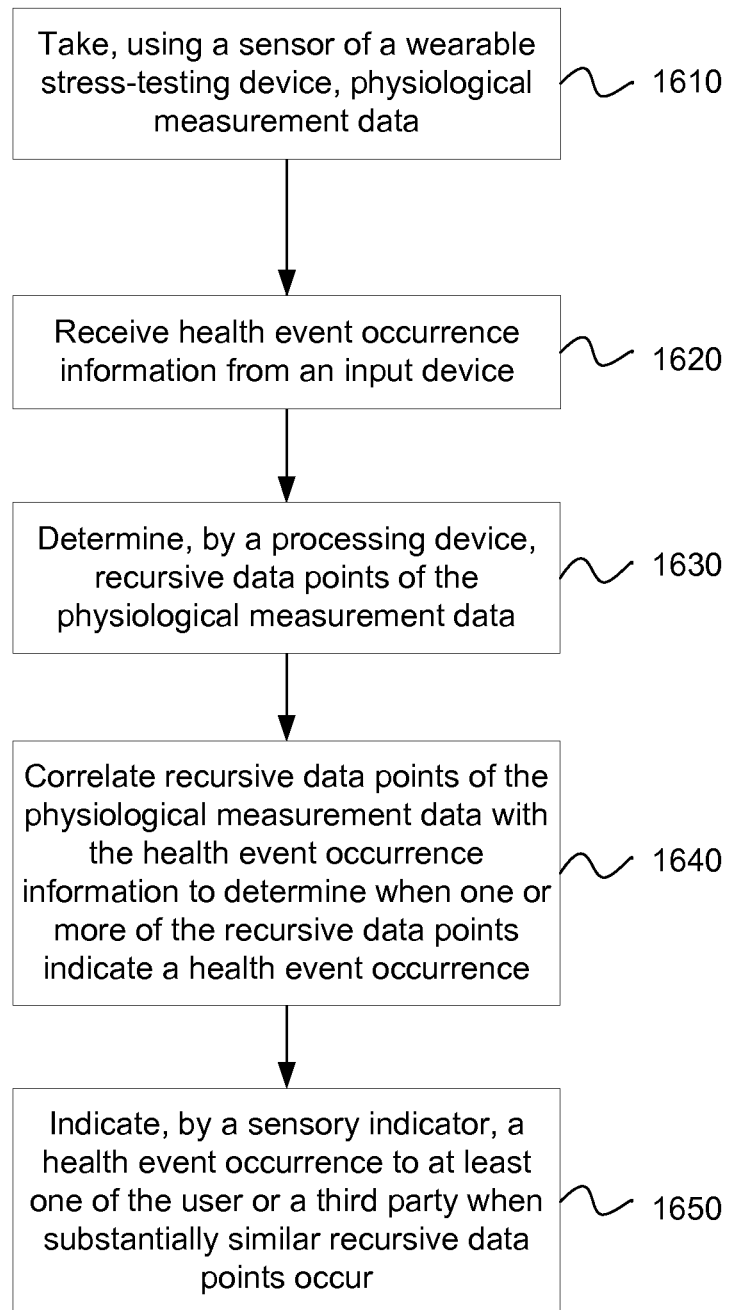
FIG. 16 depicts a flow diagram of a method for indicating a health event occurrence according to one embodiment.

FIG. 16 depicts a flow diagram of a method 1600 for indicating a health event occurrence according to one embodiment. Method 1600 may be performed by processing logic that may comprise hardware (e.g., circuitry, dedicated logic, programmable logic, microcode, etc.), software (such as operations being performed by the MCU), firmware or a combination thereof. In one example, method 1600 is performed by a processing device, a plurality of processing devices, a processor core, and/or a plurality of processor cores. Alternatively, other components of a computing system or software executing on the processing device may perform some or all of the operations of the method 1600.

Referring to FIG. 16, the method 1600 can begin by taking physiological measurements using a sensor of a wearable stress-testing device (block 1610). The method can include receiving health event occurrence information from an input device (block 1620). Health event occurrence information may include: a time when the user had a health event, such as a heart attack, a stroke, fainting, and so forth; a severity of the health event, and so forth. In one example the input device can be integrated into the wearable stress-testing device. In another example, the input device may be a separate device. In a further example, the input device may be received from a server. The method can further include determining, by a processing device coupled to the wearable stress-testing device, recursive measurement, or data points of the physiological measurements (block 1630). The method can include correlating, by the processing device, recursive measurement, or data points of the physiological measurements with the health event occurrence information to determine when one or more of the recursive measurement or data points indicate a health event occurrence (block 1640). The method can include indicating, by a sensory indicator, a health event occurrence to at least one of the user or a third party when substantially similar recursive measurement or data points occur (block 1650).

Normally, cardiac stress tests are performed in controlled environments and are limited to a number of types of tests. However, an individual has a unique physiology, and the body of the individual can react differently to a type of cardiac test. While an individual can be at high risk for a cardiac event under circumstances, under other circumstances, the cardiac risk may decrease and not be perceived during traditional stress tests. In one example, the wearable stress-testing device can analyze cardiac measurements for recursive measurement or data points in a cardiac measurement set and determine one or more conditions when a cardiac event can occur. For example, the wearable stress-testing device can continuously or semi-continuously take cardiac measurements using one or more sensors of the wearable stress-testing device. The wearable stress-testing device can analyze the continuous or semi-continuous cardiac measurements to find recursive measurement or data points or measurement or data sets in the cardiac measurements.

In one example, the wearable stress-testing device can analyze the recursive measurement or data points or recursive measurement or measurement or data sets to determine when one or more of the recursive measurement or data points or measurement or data sets indicate a cardiac event. In one example, the wearable stress-testing device can determine when one or more of the recursive measurement or data points or measurement or data sets indicate a cardiac event using the crowdsourced data discussed in the preceding paragraphs. For example, the wearable stress-testing device can correlate crowdsourced recursive measurement or data points or recursive measurement or data sets with a cardiac event to determine when recursive measurement or data points or measurement or data sets for a user of the wearable stress-testing device indicate a cardiac event. In another example, the crowdsourced data can be used to iteratively refine, filter, and/or smooth measurement data of a user of the wearable stress-testing device.

In one example, crowdsourced data of individuals can be set as a control group, e.g., healthy individuals with no medical conditions, and the measurement or data points or measurement or data sets (such as recursive measurement or data points or measurement or data sets) can be compared with measurements of the control group to determine when a measurement or data point and/or measurement or data set indicates a cardiac event. In another example, the control group can be individuals, such as athletes, and the wearable stress-testing device can compare measurement data of a user of the wearable stress-testing device to the control group to determine a difference between the data of the control group and the data of the individual. In another example, when the wearable stress-testing device determines the recursive measurement or data points or recursive measurement or data sets that signify a cardiac event may be occurring, the wearable stress-testing device can indicate to a user of the wearable stress-testing device and/or a third party when the same or substantially similar recursive measurement or data points or recursive measurement or data sets may be occurring in real-time or have previously occurred within a period of time. One advantage of analyzing the cardiac measurement data for recursive measurement or data points or recursive measurement or data sets can be to determine the conditions or events that provoke a cardiac event. For example, while jogging on a treadmill or climbing steps may not stress an individual's body to cause a cardiac event, lifting heavy objects can cause an individual's body to enter into a cardiac event. The wearable stress-testing device can analyze the recursive measurement or data points or recursive measurement or data sets to determine that when an individual lifts heavy objects a cardiac event occurs.

In one example, when the wearable stress-testing device can determine the severity of a cardiac event by comparing the cardiac measurements to a baseline cardiac measurement or data point. In one example, the baseline cardiac measurement or data point can be a previous measurement or data point in measurements of the user of the wearable stress-testing device. In another example, the baseline cardiac measurement or data point can be an average measurement or data point of crowdsourced data. In another example, the baseline cardiac measurement or data point can be a combination of the previous measurement or data point in measurements of the user of the wearable stress-testing device and the average measurement or data point of crowdsourced data. In one example, the wearable stress-testing device can compare real-time or substantially real-time data or measurements from the wearable stress-testing device with the baseline cardiac measurement or data point.

In one example, when the wearable stress-testing device determines that a cardiac event may be occurring or has occurred within a threshold period of time and the severity of a cardiac event exceeds a threshold value, the wearable stress-testing device can alert the user of the wearable stress-testing device and/or a third party (such as a caregiver, medical professional, or a family member) of the cardiac event, such as by using a sensor indicator. In one example, when the severity of a cardiac event exceeds a threshold value, the wearable stress-testing device can indicate to the user or a third party for the user to take medication, such as aspirin or nitroglycerin, and/or seek medical attention.

In another example, when the severity of a cardiac event exceeds a threshold value, the wearable stress-testing device can send a warning signal to another device. For example, when the user is driving a motor vehicle and experiences a cardiac event where the severity of a cardiac event exceeds a threshold value, the wearable stress-testing device can send a warning signal to the motor vehicle to stop the vehicle or pull the vehicle over to the side of the road. In another example, when a user experiences a cardiac event where the severity of a cardiac event exceeds a threshold value, the wearable stress-testing device can send a warning signal to a cellphone to dial an emergency number, such as 911, and communicate a predetermined message to an emergency operator, such as the problem the user may be experiencing (e.g., a stroke or heart attack) and the location of the user.

In one example the wearable stress-testing device can communicate to a third party or another device an alert using a communications network. In another example, the communications network can be a cellular network that may be a 3GPP® LTE® Rel. 8, 9, 10, 11, or 12 or IEEE® 802.16p, 802.16n, 802.16m-2011, 802.16h-2010, 802.16j-2009, 802.16-2009, and so forth. In another example, communications network can be a wireless network (such as a wireless fidelity network (Wi-Fi®) that may follow a standard such as the IEEE® 802.11-2012, IEEE® 802.llac, or IEEE® 802.llad standard. In another example, the communications network can be a Bluetooth® connection such as Bluetooth® v1.0, Bluetooth® v2.0, Bluetooth® v3.0, or Bluetooth® v4.0. In another example, the communications network can be a Zigbee® connection such as IEEE® 802.15.4-2003 (Zigbee® 2003), IEEE® 802.15.4-2006 (Zigbee® 2006), IEEE® 802.15.4-2007 (Zigbee® Pro). For example, the wearable stress-testing device can use the communications network to send an alert to another device, such as a smartphone or computer. In another example, the wearable stress-testing device can send an automated message to the third party, such as a 911 emergency operator, using the communications network. In another example, the wearable stress-testing device can communicate measurements to a third party or another device.

Figure 17:
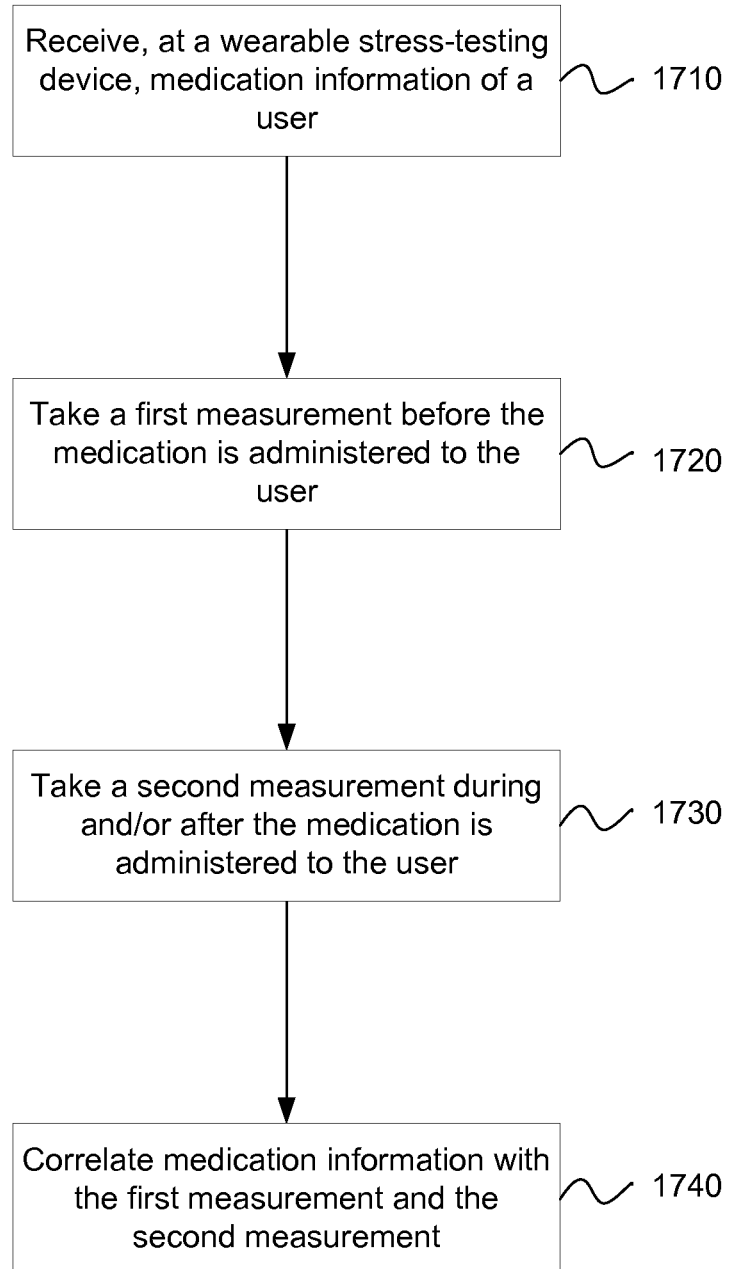
FIG. 17 depicts a flow diagram of a method for correlating medication information with a measurement according to one embodiment.

FIG. 17 depicts a flow diagram of a method 1700 for correlating medication information with a measurement according to one embodiment. Method 1700 may be performed by processing logic that may comprise hardware (e.g., circuitry, dedicated logic, programmable logic, microcode, etc.), software (such as operations being performed by the MCU), firmware or a combination thereof. In one example, method 1700 is performed by a processing device, a plurality of processing devices, a processor core, and/or a plurality of processor cores. Alternatively, other components of a computing system or software executing on the processing device may perform some or all of the operations of the method 1700.

Referring to FIG. 17, the method 1700 can begin by receiving, at a wearable stress-testing device, medication information of a user (block 1710). The method can include, taking a first measurement before the medication may be administered to the user (block 1720). The method can further include taking a second measurement during and/or after the medication is administered to the user (block 1730). The method can include correlating, by a processing device coupled to a wearable stress-testing device, medication information with the first measurement and the second measurement to determine at least one of a side effect of the medication, efficacy of the medication, or when the medication takes effect (block 1740). In one example, the method can include comparing, by a processing device, the first measurement and the second measurement to determine a change in the measurements. In this example, the processing device can determine a side effect of the medication, efficacy of the medication, or when the medication takes effect based on the change between the first measurement and the second measurement Normally, for a cardiac stress test, a patient does not take medication, as the medication can interfere with the cardiac stress test. In one example, the wearable stress-testing device can take cardiac stress measurements while a user may be taking medication or may be on medication. In one example, a user and/or physician may enter the medication information in a graphical user interface of the wearable stress-testing device. In another example, the medication information may be entered by a user and/or physician into a separate device that may be in direct or indirect communication with the wearable stress-testing device. One advantage of using the wearable stress-testing device to take cardiac stress measurements while a user is taking or on medication can be that medication may not interfere with the cardiac stress measurements. For example, a user of the wearable stress-testing device may regularly take heart medication. As the wearable stress-testing device can take cardiac stress measurements for an extended period of time and/or for a plurality of exertion events, the medication may not interfere with the cardiac stress measurements in aggregate as the effects of the medication can be filtered out by the wearable stress-testing device. In this example, the wearable stress-testing device can filter out the effects based on measurements for different exertion activities and/or by filtering out any false positives from the effects of the medication. The effects of the medication can normalize over time and the wearable stress-testing device can filter out the effects and/or adjust for the effects of the medication when taking cardiac stress measurements.

In another example, the wearable stress-testing device can measure the cardiac stress to the body of a user caused by different medication. For example, the wearable stress-testing device can take cardiac stress measurements for a period of time before the user takes medication. After the user takes medication, the wearable stress-testing device can continue to take cardiac stress measurements. The wearable stress-testing device can compare the cardiac stress measurements taken before the user took the medication and cardiac stress measurements taken after the user took the medication to determine how the body of the user reacted to the medication.

In one example, the wearable stress-testing device can receive medication user information of a user of the wearable stress-testing device using a GUI. In another example, the wearable stress-testing device can receive medication information of a user of the wearable stress-testing device from another device. In another example, the wearable stress-testing device can receive medication user information of a user of the wearable stress-testing device using a communications network.

In one example, the wearable stress-testing device can correlate the medication information with the cardiac measurement information to determine the side effects of the medication. In one example, the medication information can include the type of medication the user may be taking, when the user may be taking the medication, the amount of medication the user may be taking, and so forth. In one example, the wearable stress-testing device can use the medication information to determine cardiac side effects of the medication. In another example, the wearable stress-testing device can compare cardiac measurement information of the user from before the user began taking the medication to cardiac measurement information of the user after the user takes the medication. For example, when a user begins taking anti-depression medication, the wearable stress-testing device can compare stored cardiac measurement information of the user from before the user took the anti-depression medication with cardiac measurement information after the user began taking anti-depression medication to determine when the anti-depression medication may change how the cardiac system of the user reacts to the activities.

In one example, the wearable stress-testing device can correlate the medication information with the cardiac measurement information to determine the efficacy of the medication.

In one example, the wearable stress-testing device can continuously monitor the cardiac measurement information of the user of the wearable stress-testing device to determine a change in the cardiac measurement information after the user has taken a medication dose. For example, the user can begin using a blood pressure medication to lower high blood pressure of the user. In one example, the wearable stress-testing device can detect a change in the blood pressure or heart rate of the individual indicating that the heart of the individual does not have to work as hard to pump blood as compared to before the individual took the blood pressure medication, e.g., that the medication may be effective at lowering blood pressure for the individual. In another example, the wearable stress-testing device can detect no change in the blood pressure or heart rate of the individual indicating that the heart of the individual has to work as hard to pump blood as compared to before the individual took the blood pressure medication, e.g., that the medication may not be effective at lowering blood pressure for the individual. In another example, an individual can be taking medication, such as blood thinner medication or blood pressure medication, and the wearable stress-testing device can monitor a reaction of a body of the individual to the medications by tracking the time of day and dosage of the medication and how the heart and body react to the medication.

In one example, the wearable stress-testing device can correlate the medication information with the cardiac measurement information to determine the efficacy of non-cardiac medication. For example, a congestive heart failure patient can take fluid management medication and the wearable stress-testing device can monitor a change in a bodily system of the patient to determine the effectiveness of the fluid management medication.

In another example, the wearable stress-testing device can monitor the cardiac measurement information of the individual to determine when medicine may have an adverse side effect on a system of the individual. For example, the individual can begin taking anti-depression medication and the medication can raise the blood pressure of the individual and increase the likelihood of a stroke of the individual. The wearable stress-testing device can monitor the cardiac measurement information of the user of the wearable stress-testing device to determine that a side effect of the anti-depression medication may be an increase in the blood pressure and cardiac stress on the individual. In another example, the wearable stress-testing device can monitor the cardiac measurement information of the individual in real time to determine when a medication begins to take effect. In one example, the wearable stress-testing device can monitor when a medication begins to take effect to determine a medication dosage correction. In one example, the wearable stress-testing device can determine the rate that a body of a user of the wearable stress-testing device can metabolized medication based on when the medication was taken and when the medication begins to take effect. For example, when an individual may be at high risk of a cardiac event, such as a heart attack, the individual may carry around nitroglycerin for when a cardiac event occurs. The wearable stress-testing device can indicate to the user when a cardiac event occurs, and the individual can take nitroglycerin medication. When the user takes the nitroglycerin medication, the wearable stress-testing device can monitor the reaction of the body of the user to determine the effectiveness of the nitroglycerin medication and/or indicate when an increased dosage may be required to counteract the cardiac event.

In one example, the wearable stress-testing device can monitor the cardiac measurement information for a period of time using the wearable stress-testing device to determine when a treatment regiment, e.g., multiple rounds taking medication, may be effective for treating the individual. In one example, the wearable stress-testing device can perform a trend analysis for the cardiac measurement information for the period of time to determine when a trend indicates that the treatment regimen may be causing the body of an individual to have a reaction, such as lowering of a heart rate or blood pressure. In another example, cardiac measurement information of the wearable stress testing device can be communicated to a medical professional in real-time or at times using a telemedicine system. In one example, the telemedicine system can communicate cardiac measurement information of the user to the medical professional to enable the medical professional to analyze the cardiac measurement information of the user of the wearable stress-testing device. One advantage of communicating the cardiac measurement information of the wearable stress-testing device to the medical professional in real-time using the telemedicine system may be that the medical professional can continuously or periodically monitor the user without having to meet face-to-face. In one example, the medical professional can request that the individual perform activities in real-time and monitor the measurement information of the individual to determine the medical status of the individual without the individual coming in for a doctor visit. The medical professional can monitor when a medical event risk may be increasing or decreasing while enabling the user to continue the daily activities of the user.

In one example, the wearable stress-testing device can determine that the user of the wearable stress-testing device may be having a cardiac event when the user of the wearable stress-testing device may be relatively inactive or at a low activity level and the cardiac measurement information indicates that the cardiac system of the individual may be experiencing a high level of stress.

Figure 18:
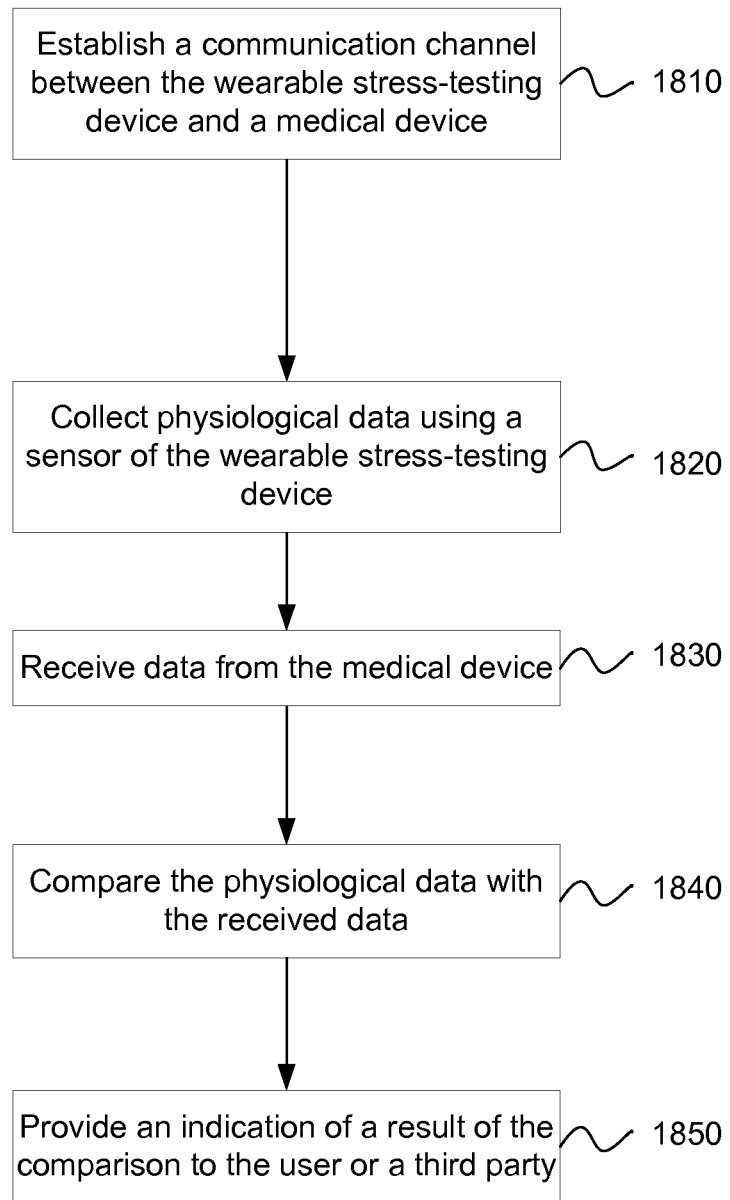
FIG. 18 depicts a flow diagram of a method providing an indication of a comparison according to one embodiment.

FIG. 18 depicts a flow diagram of a method 1800 providing an indication of a result of a comparison according to one embodiment. Method 1800 may be performed by processing logic that may comprise hardware (e.g., circuitry, dedicated logic, programmable logic, microcode, etc.), software (such as operations being performed by the MCU), firmware or a combination thereof. In one example, method 1800 is performed by a processing device, a plurality of processing devices, a processor core, and/or a plurality of processor cores. Alternatively, other components of a computing system or software executing on the processing device may perform some or all of the operations of the method 1800.

Referring to FIG. 18, the method 1800 can begin by establishing a communication channel between the wearable stress-testing device and a medical device (block 1810). In one example, the communication channel can be established by pairing of the wearable stress-testing device. In another example, the communication channel can be established using a communication protocol, such as a cellular communication protocol. The method can include, collecting physiological measurements using a sensor of the wearable stress-testing device (block 1820). The method can further include receiving measurements from the medical device (block 1830). The method can further include comparing, by a processing device coupled to the wearable stress-testing device, the physiological measurements with the received data to determine that the medical device is functioning properly, to determine a medical diagnosis, and/or to determine a change in a system of a user based on physiological changes of the user (block 1840). The method can include providing an indication of a result of the comparison to the user or a third party (block 1850).

In one example, the wearable stress-testing device can be paired with a medical device to determine when then medical device may be functioning properly or may be malfunctioning. For example, the user of the wearable stress-testing device can have a pacemaker. The wearable stress-testing device can be paired with the pacemaker to monitor when the pacemaker may be providing the heart of the individual with the correct cardiac rhythm to enable the cardiac system of the individual to function properly. In one example, the wearable stress-testing device can receive the cardiac rhythm of the pacemaker and compare the cardiac rhythm of the pacemaker with the cardiac measurement information of the wearable stress-testing device to determine that the pacemaker may be functioning properly or that the pacemaker may be malfunctioning. In one example, when the wearable stress-testing device determines that the paired medical device, such as the pacemaker, may be malfunctioning, the wearable stress-testing device can indicate to the user of the wearable stress-testing device or a third party that the paired medical device may be malfunctioning.

In another example, the paired medical device can communicate additional measurement information that can be correlated with the cardiac measurement information from the wearable stress-testing device. For example, the paired medical device can monitor the hydration level of the individual. The wearable stress-testing device can correlate the hydration level of the individual to determine the effect of physiological changes of the individual, such as dehydration, on the cardiac system of the individual.

In another example, the wearable stress-testing device can correlate physiological changes of the individual with the cardiac measurement information from the wearable stress-testing device to determine medical diagnosis. For example, the wearable stress-testing device can monitor the cardiac system of the individual and the medical device can monitor the hydration level of the individual. The wearable stress-testing device can correlate an increase in the hydration level of the individual and an increased cardiac stress level with a congestive heart failure event of the individual. In another example, the medical device can communicate to the wearable stress-testing device a medical event indicator to signal when the individual may be experiencing a medical event, such as a congestive heart failure event. When the wearable stress-testing device receives the medical event indicator, the wearable stress-testing device can begin recording and/or storing the cardiac measurements and/or mark the time in the cardiac measurements when the medical event began. One advantage of storing the cardiac measurements and/or mark the time in the cardiac measurements when the medical event began may be to enable an individual and/or a third party to determine how the cardiac system of the individual reacted to the medical event, e.g., a medical professional can determine when in the cardiac measurements the medical event began. In another example, the medical event can be pneumonia. When an individual has pneumonia, the oxygen levels of the blood of the individual can decrease and the cardiac system of the individual may work harder to provide oxygen to the body of the individual. The wearable stress-testing device can determine that the stress to the cardiac system of the individual may be increasing and indicate that the individual may have a medical condition, such as pneumonia.

In one example, the wearable stress-testing device can compare a level of exertion of an individual with a cardiovascular performance of the individual. For example, the individual can be a professional athlete performing endurance training. The professional athlete can use the wearable stress-testing device to compare one or more of levels of exertion the professional athlete with the cardiovascular performance of the body of the professional athlete. One advantage of comparing the exertion level of an individual, such as a professional athlete, can be to enable the professional athlete to adjust exercises to improve cardiovascular performance for activities. In another example, the professional athlete can use the wearable stress-testing device during a cool-down exercise to determine how the cardiovascular system of the individual may be reacting to the cool down exercise. One advantage of monitoring the cardiac measurement information during a cool down exercise can be to enable an individual, such as a professional athlete, to determine the cool down exercise time period and/or one or more levels of exertion to increase the effectiveness of the cool down exercises. For example, the wearable stress-testing device can communicate cardiac measurements to the professional athlete in real-time or substantially real-time to enable the professional athlete to determine the period of time to perform one or more cool down exercises to decrease the probability of an injury.

Figure 19:
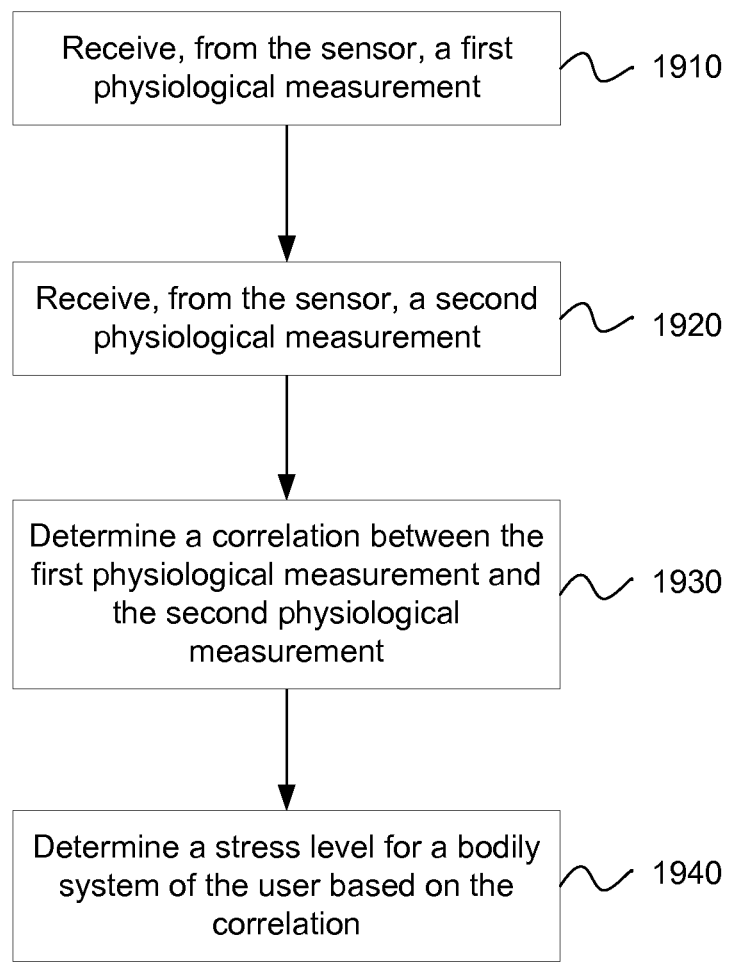
FIG. 19 depicts a flow diagram of a wearable device operable to determine a stress level of a bodily system of a user based on a correlation according to one embodiment.

FIG. 19 depicts a flow diagram 1900 of a wearable device operable to determine a stress level of a bodily system of a user based on a correlation according to one embodiment. The wearable device can include: a housing formed and shaped to affix to a user; a sensor integrated into the housing operable to engage a body of the user to take physiological measurements of the user over a threshold period of time; and a processing device coupled to the sensor; and a sensory indicator. The processing device can receive, from the sensor, a first physiological measurement (block 1910). The processing device can further receive, from the sensor, a second physiological measurement (block 1920).

The processing device can further determine a correlation between the first physiological measurement and the second physiological measurement (block 1930). The processing device can further determine a stress level for a bodily system of the user based on the correlation (block 1940). In one example, the sensory indicator can generate an indication representative of the stress level and display the indication via a display.

In one example, the processing device can: analyze the first physiological measurement and the second physiological measurement to determine an abnormality between the first physiological measurement and the second physiological measurement; determine that the abnormality is a negative abnormality; and increase the stress level based on the negative the abnormality. In another example, the processing device can receive, from a second device, a third physiological measurement over a communication network; determine a second correlation between the third physiological measurement and at least one of the first physiological measurement or the second physiological measurement; and predict a change in the stress level of the bodily system based on a change in the third physiological measurement. In another example, the processing device can: receive, from a second device, crowdsourced data over a communication network; determine a second correlation between the crowdsourced data and at least one of the first physiological measurement or the second physiological measurement; associate the second correlation with the stress level of the bodily system; and set a baseline for the stress level of the bodily system based on the second correlation.

In one example, the first physiological measurement can be a measurement of the bodily system taken at a first point in time before medication is consumed by the user; the second physiological measurement can be a measurement of the bodily system taken at a second point in time after the medication may be consumed by the user; and the processing device may further determine a change in the stress level of the bodily system from the first point in time to the second point in time. In another example, the wearable device further comprises an input device to receive a user input; and the processing device can: receive, from the input device, the user input, wherein the user input is a command to increase or decrease a sensitivity of the sensor; and adjust a sensitivity of the sensor based on the user input.

Figure 20:
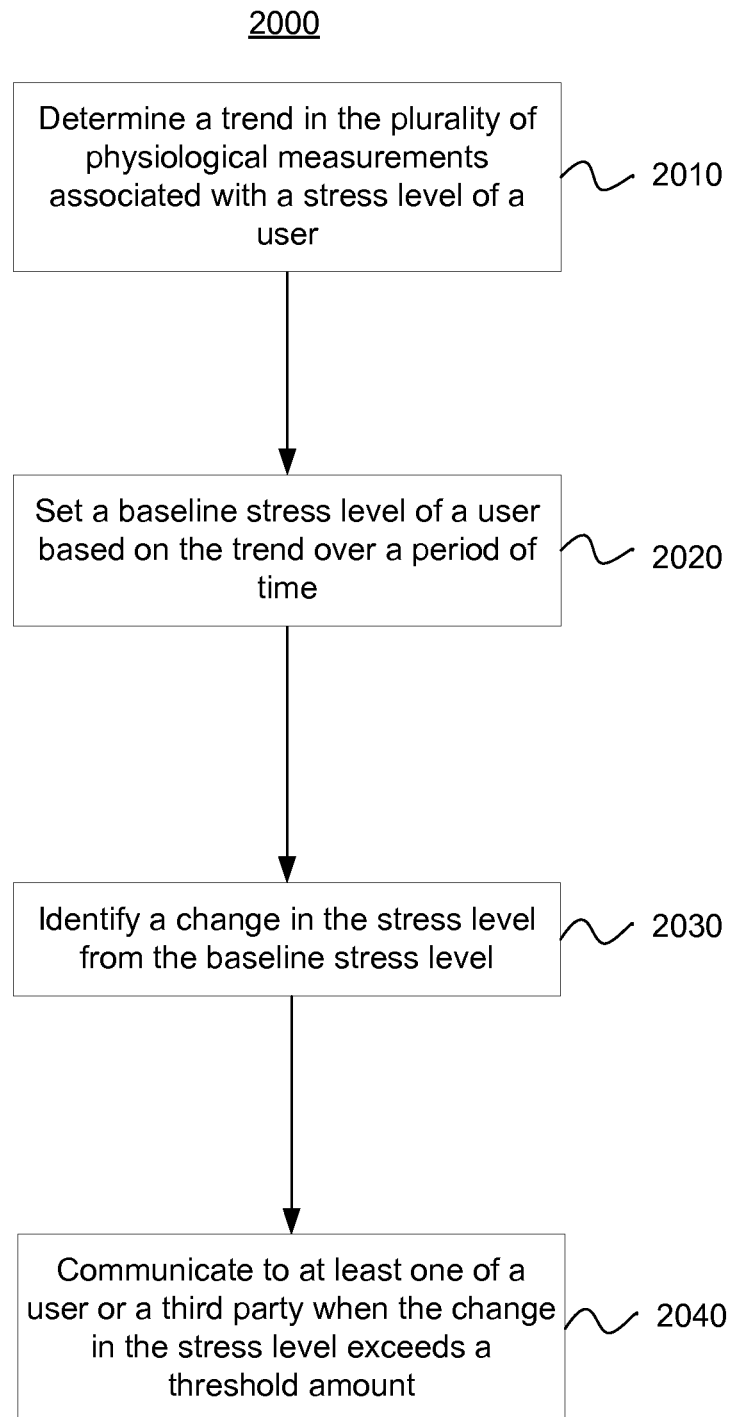
FIG. 20 depicts a flow diagram of a wearable device operable to determine a stress level of a bodily system of a user based on a trend according to one embodiment. [0024]

FIG. 20 depicts a flow diagram 2000 of a wearable device operable to determine a stress level of a bodily system of a user based on a trend according to one embodiment. The wearable device can include: a sensor interface to receive a plurality of physiological measurements; a memory device, coupled to the sensor interface, the memory device to store the plurality of physiological measurements; and a processing device coupled to the sensor interface. The processing device can be operable to determine a trend in the plurality of physiological measurements associated with a stress level of a bodily system of a user (block 2010). The processing device can further be operable to set a baseline stress level of the user based on the trend over a period of time (block 2020). The processing device can be operable to identify a change in the stress level from the baseline stress level (block 2030). The processing device can be operable communicate to at least one of a user or a third party when the change in the stress level exceeds a threshold amount (block 2040).

In one example, the sensor interface can be further operable to receive an environmental measurements; the memory device can be further operable to store the environmental measurements; and the processing device can be further operable to: determine a correlation between the trend and the environmental measurements; associate the environmental measurements with the stress level based on the correlation; and adjust the stress level of the bodily system based on a change in the environmental measurements. In another example, the processing device can be further operable to determine a direction of the trend; and set a medical status of the user based on the direction of the trend. In another example, the wearable device can be coupled to an input device; and the processing device is further operable to receive, from the input device, user information, wherein the user information comprises a medical status of the user; and set the medical status based on the user information. In another example, the wearable device further can further comprise a sensory indicator operable to generate an indication representative of the stress level; and communicate the indication representative to at least one of the user or a third party.

In one example, the processing device can further be operable to determine that the stress level exceeds a threshold level; and the sensory indicator can further be operable to communicate to the user an indication to reduce or to cease a current activity. In another example, the sensor interface can receive a movement measurement of the user; and the processing device can further be operable to determine an exertion level of the user based on the movement measurement; associate the stress level of the bodily system with the exertion level; and determine a predicted stress level of the user based on the exertion level.

Figure 21:
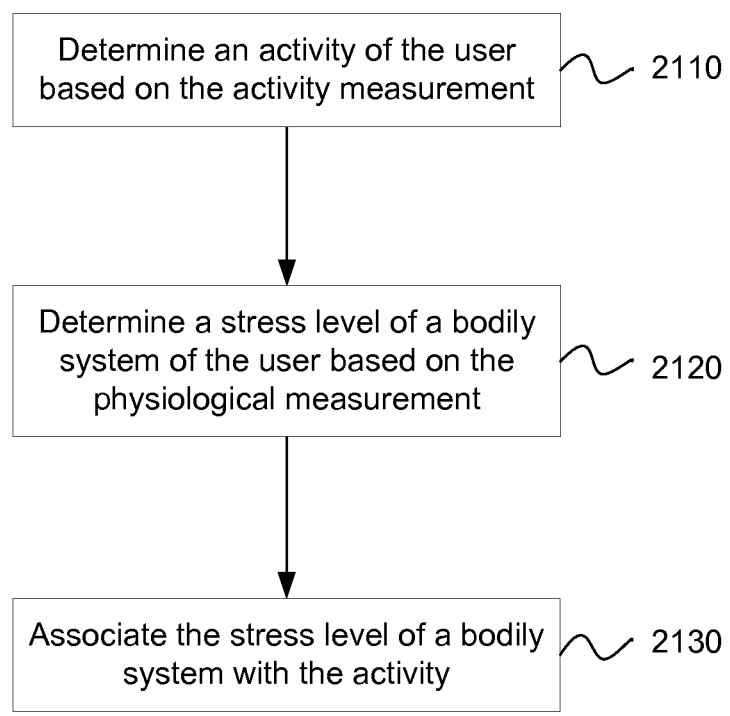
FIG. 21 depicts a flow diagram of a wearable device operable to determine a stress level of a bodily system based on physiological measurement and an activity of a user according to one embodiment.

FIG. 21 depicts a flow diagram 2100 of a wearable device operable to determine a stress level of a bodily system based on physiological measurement and an activity of a user according to one embodiment. The wearable device can include: a housing formed and shaped to affix to a user; a sensor array integrated into the housing; and a processing device coupled to the sensor array. In one example, the sensor array can include a first sensor operable take an activity measurement of the user; and a second sensor operable take a physiological measurement of the user. The processing device can be operable to determine an activity of the user based on the activity measurement (block 2110). The processing device can further be operable to determine a stress level of a bodily system of the user based on the physiological measurement (block 2120). The processing device can further be operable to associate the stress level of the bodily system with the activity (block 2130).

In one example, the processing device can further be operable to determine a stress level pattern in the physiological measurement for the activity; and predict, for the activity, a stress level of the bodily system based on the pattern. In another example, the wearable device can further be operable to generate an indication representative of the predicted stress level; and communicate the indication representative to at least one of the user or a third party. In another example, the processing device can further be operable to receive, by an input device, health event occurrence information; analyze the activity measurement and the physiological measurement to determine recursive data points in the activity measurement and the physiological measurement; and correlate the recursive data points with the health event occurrence information to determine one or more recursive data points that indicate a health event occurrence.

In one example, the first sensor can further be operable to take a plurality of activity measurement and the second sensor can further be operable to take a plurality of physiological measurements. In another example, the processing device can further: analyze the plurality of activity measurements and the plurality of physiological measurements to determine recursive data points in the plurality of physiological measurements; determine a stress level of the user for the plurality of physiological measurements; monitor for new data points that are substantially similar to the recursive data points; and predict the stress level of the user based on the new data points. In another example, the wearable device includes a communication device to establish a communication channel with a second device; and receive, from the second device, another measurement. In this example, the processing device can further compare the other measurement with the activity measurement or the physiological measurement to determine that the second device is functioning properly. In another example, the housing can be formed and shaped to affix to wrist of the user.

In the preceding paragraphs, one or more specific types of measurements may be used in an example, such as a blood pressure measurement, a heart rate measurement, a hydration level measurement, and so forth. The types of measurements and the number of measurements are not intended to be limiting, but rather for the purpose of describing particular example embodiments. Different types and number of measurements can be substituted in the examples and embodiments. The examples in the preceding paragraphs are not intended to be exhaustive or to limiting. Individual measurements, sensors, elements, or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Figure 22:
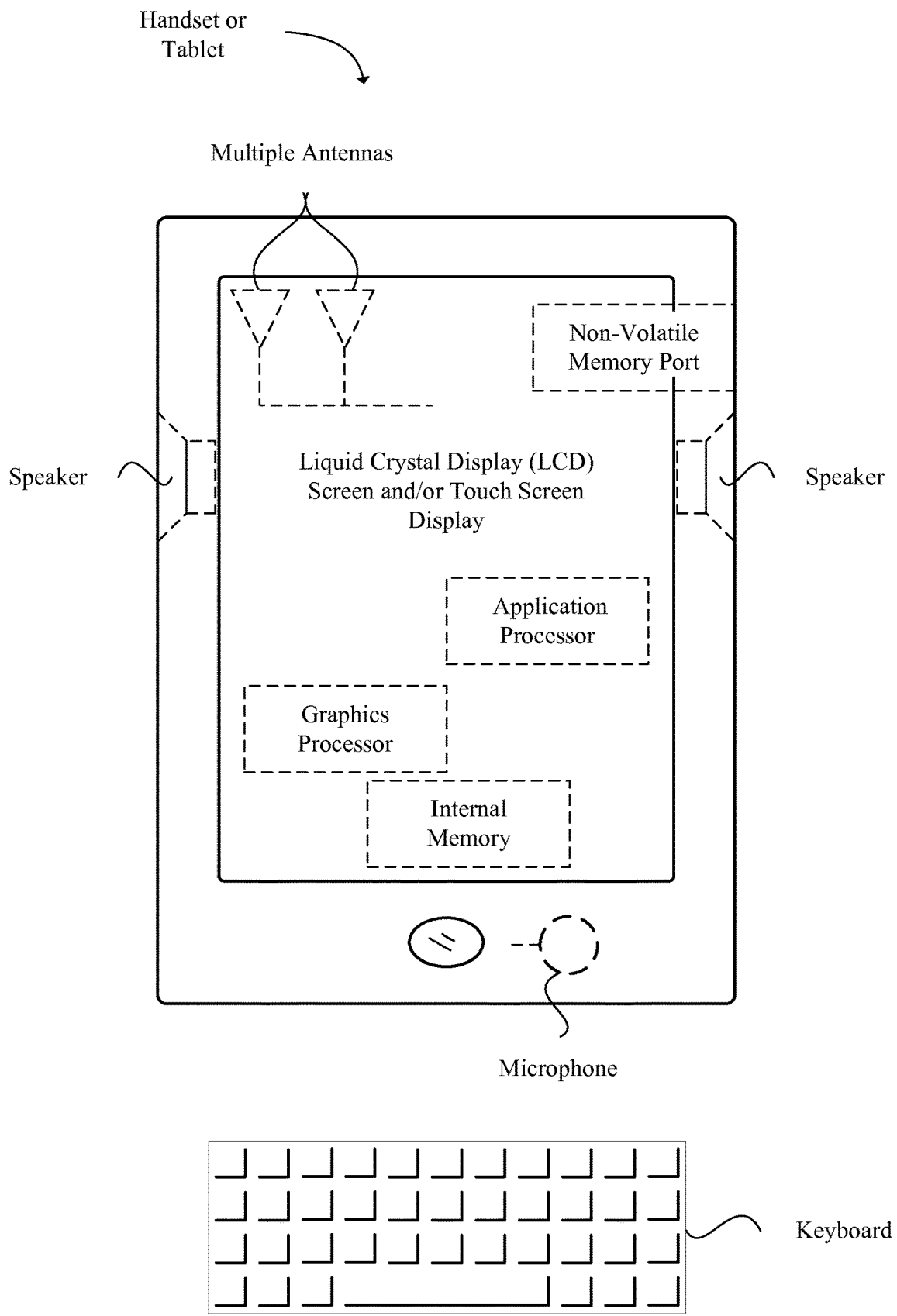
FIG. 22 provides an example illustration of a device according to one embodiment.

FIG. 22 provides an example illustration of a device according to one embodiment. The device can include a wearable device, a wearable stress-testing device, a user equipment (UE), a base station, a UMD, a mobile wireless device, a mobile communication device, a tablet, a handset, or other type of wireless device. The device can include one or more antennas configured to communicate with different devices. The device can be configured to communicate using at least one wireless communication standard including 3GPP® LTE®, WiMAX®, High Speed Packet Access (HSPA), Bluetooth®, and Wi-Fi® technologies. The device can communicate using separate antennas for each wireless communication standard or shared antennas for multiple wireless communication standards. The device can communicate in a wireless local area network (WLAN), a wireless personal area network (WPAN), and/or a WWAN.

FIG. 22 also provides an illustration of a microphone and one or more speakers that can be used for audio input and output from the device. The display screen may be a liquid crystal display (LCD) screen, or other type of display screen such as an organic light emitting diode (OLED) display. The display screen can be configured as a touchscreen. The touch screen may use capacitive, resistive, or another type of touch screen technology. An application processor and a graphics processor can be coupled to internal memory to provide processing and display capabilities. A non-volatile memory port can also be used to provide data input/output options to a user. The non-volatile memory port may also be used to expand the memory capabilities of the wireless device. A keyboard may be integrated with the wireless device or wirelessly connected to the wireless device to provide additional user input. A virtual keyboard may also be provided using the touch screen.

Various techniques, or certain aspects or portions thereof, may take the form of program code (i.e., instructions) embodied in tangible media, such as floppy diskettes, CD-ROMs, hard drives, non-transitory computer readable storage medium, or any other machine-readable storage medium where, when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a RAM, EPROM, flash drive, optical drive, magnetic hard drive, or other medium for storing electronic data. The base station and mobile station may also include a transceiver module, a counter module, a processing module, and/or a clock module or timer module. One or more programs that may implement or utilize the various techniques described herein may use an application programming interface (API), reusable controls, and the like. Such programs may be implemented in a high-level procedural or object-oriented programming language to communicate with a computer system. However, the program(s) may be implemented in assembly or machine language, if desired. In any case, the language may be a compiled or interpreted language, and combined with hardware implementations.

It should be understood that many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module need not be physically located together but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single measurement or data set or may be distributed over different locations including over different storage devices, and may exist, at least partially, merely as electronic signals on a system or network. The modules may be passive or active, including agents operable to perform desired functions.

Reference throughout this specification to "an example" means that a particular feature, structure, or characteristic described in connection with the example is included in at least one embodiment of the present invention. Thus, appearances of the phrases "in an example" in various places throughout this specification are not necessarily all referring to the same embodiment.

As used herein, multiple items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as defacto equivalents of one another but are to be considered as separate and autonomous representations of the present invention.

Furthermore, the described features, structures, or characteristics may be combined in any suitable manner in one or more embodiments. In the foregoing description, numerous specific details are provided, such as examples of layouts, distances, network examples, etc., to provide a thorough understanding of embodiments of the invention. One skilled in the relevant art will recognize, however, that the invention can be practiced without one or more of the specific details, or with other methods, components, layouts, etc. In other instances, well-known structures, materials, or operations are not shown or described in detail to avoid obscuring aspects of the invention.

While the foregoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

Figure 23:
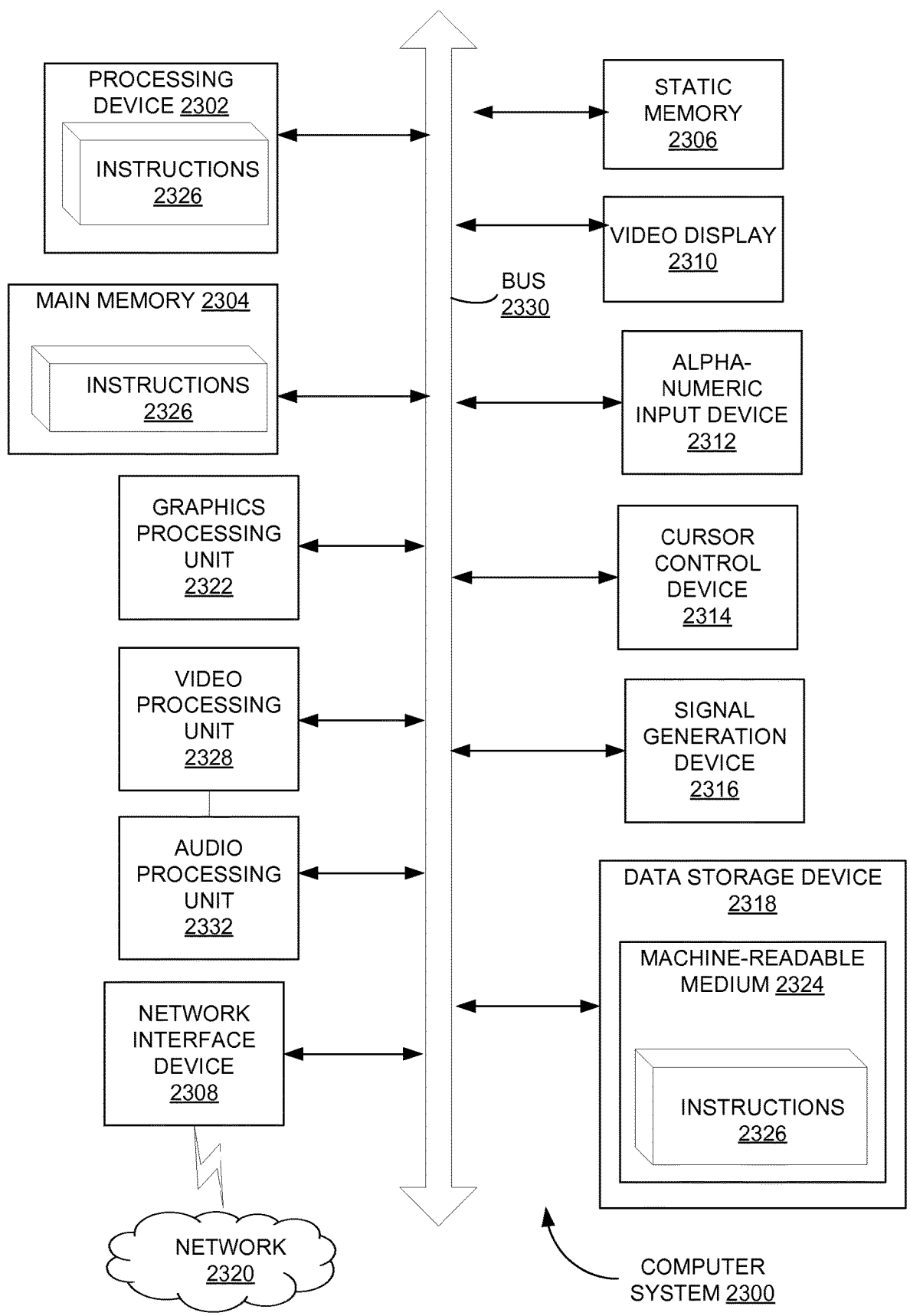
FIG. 23 illustrates a diagrammatic representation of a machine in the exemplary form of a computer system within which a set of instructions for causing the machine to perform any one or more of the methodologies discussed herein, may be executed.

FIG. 23 illustrates a diagrammatic representation of a machine in the exemplary form of a computer system 2300 within which a set of instructions for causing the machine to perform any one or more of the methodologies discussed herein, may be executed. In alternative implementations, the machine may be connected (e.g., networked) to other machines in a LAN, an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The exemplary computer system 2300 includes a processing device (processor) 2302, a main memory 2304 (e.g., read-only memory (ROM), flash memory, dynamic random-access memory (DRAM) such as synchronous DRAM (SDRAM) or Rambus DRAM (RDRAM), etc.), a static memory 2306 (e.g., flash memory, static random-access memory (SRAM), etc.), and a data storage device 2318, which communicate with each other via a bus 2330.

Processing device 2302 represents one or more general-purpose processing devices such as a microprocessor, central processing unit, or the like. More particularly, the processing device 2302 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 2302 may also be one or more special-purpose processing devices such as an application specific integrated circuit (ASIC), a field programmable gate array (FPGA), a digital signal processor (DSP), network processor, or the like. The processing device 2302 is configured to execute instructions 2326 for performing the operations and steps discussed herein.

The computer system 2300 may further include a network interface device 2322. The computer system 2300 also may include a video display unit 2310 (e.g., a liquid crystal display (LCD), a cathode ray tube (CRT), or a touch screen), an alphanumeric input device 2312 (e.g., a keyboard), a cursor control device 2314 (e.g., a mouse), and a signal generation device 2316 (e.g., a speaker). The computer system 2300 may further include a video processing unit 2328 and an audio processing unit 2332.

The data storage device 2318 may include a machine-readable storage medium 2324 on which is stored one or more sets of instructions 2326 (e.g., software) embodying any one or more of the methodologies or functions described herein. The instructions 2326 may also reside, completely or at least partially, within the main memory 2304 and/or within the processing device 2302 during execution thereof by the computer system 2300, the main memory 2304 and the processing device 2302 also constituting computer-readable storage media. The instructions 2326 may further be transmitted or received over a network 2320 via the network interface device 2334.

While the machine-readable storage medium 2324 is shown in an exemplary implementation to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding, or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

In the foregoing description, numerous details are set forth. It will be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure.

Some portions of the detailed description have been presented in terms of algorithms and symbolic representations of operations on data bits within a computer memory. These algorithmic descriptions and representations are the means used by those skilled in the data processing arts to convey the substance of their work most effectively to others skilled in the art. An algorithm is here, and generally, conceived to be a self-consistent sequence of steps leading to a desired result. The steps are those having physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "segmenting", "analyzing", "determining", "enabling", "identifying," "modifying" or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The disclosure also relates to an apparatus for performing the operations herein. This apparatus may be specially constructed for the required purposes, or it may include a general-purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such.

Reference throughout this specification to "one embodiment" or "an embodiment" means that a particular feature, structure, or characteristic described in connection with the embodiment is included in at least one embodiment. Thus, the appearances of the phrase "in one embodiment" or "in an embodiment" in various places throughout this specification are not necessarily all referring to the same embodiment. In addition, the term "or" is intended to mean an inclusive "or" rather than an exclusive "or."

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

The invention claimed is:

1. A wearable device comprising:
a housing shaped to be coupled to a user;
a sensor integrated into the housing, wherein:
the sensor is operable to continuously or semi-continuously detect a vascular measurement of the user and, when operating semi-continuously, the sensor comprises measurement instants, wherein the measurement instants comprise recursive vascular measurements to monitor changes in a physiological condition corresponding to a vascular event, and wherein the sensor comprises:
an oxygen saturation sensor,
a respiration sensor,
a breath rate sensor, or
a cardiac sensor, and
the sensor comprises one sensor or an array of sensors; and
a processing device coupled to the sensor, wherein the processing device is operable to:
receive a first set of vascular measurement data associated with a first physical activity of the user, wherein the first set of vascular measurement data is captured by the sensor;
identifying a first data pattern in the first set of vascular measurement data as corresponding to the vascular event;
adjust the processing device to a data scrutiny level based on health risk information for the user, wherein the data scrutiny level includes a high data scrutiny level, a normal data scrutiny level, or a low data scrutiny level;
in response to identifying the first data pattern as corresponding to a vascular event, receive verification data from a non-continuous measurement device to verify that the user is undergoing the vascular event; and
in response to:

verifying that the user is undergoing the vascular event via the noncontinuous measurement device, tag the first data pattern as corresponding to the vascular event; or verifying that the user is not undergoing the vascular event based on data received from the non-continuous measurement device, indicate that the first data pattern does not correspond to the vascular event.

2. The wearable device of claim 1, wherein the processing device is further configured to:

determine a precursive event pattern; and predict a second vascular event of a body of the user based on the precursive event pattern.

3. The wearable device of claim 2, wherein the wearable device is further to:

generate an indication representative of the vascular event; and communicate the indication to a device associated with the user or a third party.

4. The wearable device of claim 1, wherein the processing device is further to:

receive, by an input device, health event occurrence information;

analyze the first set of vascular measurement data and a second set of vascular measurement data to determine recursive data points between the first set of vascular measurement data and the second set of vascular measurement data; and correlate the recursive data points of the health event occurrence information with the recursive data points between the first set of vascular measurement data and the second set of vascular measurement data to identify one or more common recursive data points that indicate a health event occurrence of the vascular event.

5. The wearable device of claim 4, wherein:

the sensor is further operable to:

take the first set of vascular measurement data for a first type of activity; and take the second set of vascular measurement data for a second type of activity; and the processing device is further configured to:

determine a correlation between the first type of activity and the second type of activity based on the recursive data points between the first set of vascular measurement data and the second set of vascular measurement data;

identify subsequent data points of a subsequent vascular measurement that are substantially similar to the recursive data points; and predict another vascular event of a body of the user based on the subsequent data points.

6. The wearable device of claim 1, wherein:

the wearable device further comprises a communication device to:

establish a communication channel with a second device; and receive, from the second device, a third set of vascular measurement data; and the processing device is further configured to compare the third set of vascular measurement data with the first set of vascular measurement data to determine that the wearable device is functioning properly.

7. The wearable device of claim 6, wherein the processing device is further configured to calibrate the wearable device based on the comparison of the of the third set of vascular measurement data with the first set of vascular measurement data.

8. A system comprising:

a non-continuous measurement device configured to detect a first non-continuous exercise measurement of a user;

a wearable device shaped to be coupled to the user, the wearable device comprising:

a sensor configured to detect a exercise measurement of the user;

wherein the sensor is operable to continuously or semi-continuously detect a vascular measurement of the user, the sensor comprising:

an oxygen saturation sensor, a respiration sensor, a breath rate sensor, or a cardiac sensor, the sensor comprises one sensor or an array of sensors; and a processing device coupled to the sensor, wherein the processing device is configured to:

receive a first set of exercise measurement data associated with a first physical activity of the user, wherein the first set of exercise measurement data is captured by the sensor;

calibrate the wearable device by comparing the first set of exercise measurement data from the wearable device with the first non-continuous exercise measurement from the noncontinuous measurement device;

identify a first data pattern in the first set of exercise measurement data as corresponding to a cardiovascular event;

adjust the processing device to a data scrutiny level based on the identification of the first data pattern, wherein the data scrutiny level includes a high data scrutiny level, a normal data scrutiny level, or a low data scrutiny level; and in response to identifying the first data pattern as corresponding to the cardiovascular event, receive a second non-continuous measurement from the non-continuous measurement device to verify that the user is undergoing the cardiovascular event; and in response to verifying that the user is undergoing the cardiovascular event based on the non-continuous measurement device, communicate an indication of the cardiovascular event via a display of the wearable device.

9. The system of claim 8, wherein the processing device is further configured to:

receive, from a device, crowdsourced data over a communication network; and compare the first set of exercise measurement data to the crowdsourced data to further verify that the user is undergoing the cardiovascular event.

10. The system of claim 8, wherein the processing device is further configured to determine a stress level of the user based on the first set of exercise measurement data.

11. The system of claim 8, wherein the processing device is further configured to further identify the cardiovascular event based on an environmental measurement detected by the sensor of the wearable device.

12. The system of claim 11, wherein the processing device is further configured to determine the environmental condition based on at least one of a temperature, pressure, or humidity measurement.

13. The system of claim 8, wherein the processing device is further configured to predict the cardiovascular event based on detection of an event precursor in the first data pattern.

14. The system of claim 13, wherein the processing device is further configured to communicate an indication to the user to discontinue the first physical activity in response to the detection of the event precursor in the first data pattern.

15. A method comprising:
receiving, by a wearable device, a first set of health measurement data associated with a first physical activity of a user, wherein the first set of health measurement data is captured by a sensor of the wearable device wherein:
the sensor is operable to continuously or semi-continuously detect a health measurement of the user, comprising:
an oxygen saturation sensor,
a respiration sensor,
a breath rate sensor, or
a cardiac sensor,
the sensor comprises one sensor or an array of sensors; and
performing, by the wearable device, a calibration of the wearable device by comparing the first set of health measurement data from the wearable device with a first non-continuous health measurement from a non-continuous measurement device;
identifying a first data pattern in the first set of health measurement data as corresponding to a health risk;
adjust a processing device to a data scrutiny level based on the identification of the first data pattern, wherein the data scrutiny level includes a high data scrutiny level, a normal data scrutiny level, or a low data scrutiny level; and
in response to identifying the first data pattern as corresponding to a health risk, receiving a second non-continuous measurement from the non-continuous measurement device to verify that the user is undergoing the health risk; or
in response to verifying the user's health risk based on the non-continuous measurement device, communicating an indication of the health risk to the user via a display of the wearable device.

16. The method of claim 15, further comprising:
receiving, by the sensor of the wearable device, a second set of health measurement data associated with a second physical activity of the user; and
predicting, by the processing device of the wearable device, another health risk based on a comparison of the second set of health measurement data with the first set of health measurement data.

17. The method of claim 15, further comprising communicating an indication to the user of the predicted health risk.

18. The method of claim 15, further comprising establishing, by the wearable device, an individualized baseline from health measurement data not corresponding with the health risk, wherein the individualized baseline is unique to the user.

19. The method of claim 18, wherein verifying that the user is undergoing the health risk further comprises comparing the first set of health measurement data to the individualized baseline.

20. The method of claim 15, further comprising communicating to the user, by the wearable device, a recommendation to reduce or to cease the first physical activity in response to verifying that the user is undergoing the health risk.

* * * * *